(12) United States Patent
Fischer

(10) Patent No.: US 6,585,513 B2
(45) Date of Patent: Jul. 1, 2003

(54) ENDODONTIC SYSTEMS AND METHODS FOR PREPARING APICAL PORTIONS OF ROOT CANALS WITH A SET OF FILES HAVING LARGE TAPERS

(75) Inventor: Dan E. Fischer, Sandy, UT (US)

(73) Assignee: Ultradent Products, Inc., South Jordan, UT (US)

( * ) Notice: Subject to any disclaimer, the term of this patent is extended or adjusted under 35 U.S.C. 154(b) by 3 days.

(21) Appl. No.: 09/848,053

(22) Filed: May 3, 2001

(65) Prior Publication Data

US 2002/0037492 A1 Mar. 28, 2002

Related U.S. Application Data

(63) Continuation-in-part of application No. 09/736,729, filed on Dec. 14, 2000, and a continuation-in-part of application No. 09/753,981, filed on Jan. 3, 2001, now Pat. No. 6,390,819, which is a continuation-in-part of application No. 09/536,821, filed on Mar. 27, 2000, now Pat. No. 6,379,155, which is a continuation-in-part of application No. 09/492,566, filed on Jan. 27, 2000, now Pat. No. 6,217,335, which is a continuation-in-part of application No. 09/325,035, filed on Jun. 3, 1999, now Pat. No. 6,059,572.

(51) Int. Cl.[7] .................................................. A61C 5/02

(52) U.S. Cl. ...................................... 433/224; 433/102

(58) Field of Search ................................ 433/224, 102, 433/81

(56) References Cited

U.S. PATENT DOCUMENTS

| | | |
|---|---|---|
| 322,265 A | 7/1885 | Donaldson |
| 621,873 A | 3/1899 | Vajna |
| 1,168,052 A | 1/1916 | Bolls |
| 1,369,112 A | 2/1921 | Jones |
| 3,715,331 A | 2/1973 | Molnar .................. 260/41 |
| 3,807,048 A | 4/1974 | Malmin .................. 32/40 R |
| 3,925,895 A | 12/1975 | Kliment et al. .............. 32/15 |
| 3,959,212 A | 5/1976 | Rockett et al. ........... 260/42.53 |
| 4,019,254 A | 4/1977 | Malmin ..................... 32/57 |
| 4,190,958 A | 3/1980 | Martin et al. .............. 433/102 |
| 4,231,738 A | 11/1980 | Riitano et al. ............. 433/102 |
| 4,332,561 A | 6/1982 | McSpadden ............... 433/102 |
| 4,353,696 A | 10/1982 | Bridges .................... 433/125 |
| 4,364,730 A | 12/1982 | Axelsson .................. 433/141 |
| 4,466,795 A | 8/1984 | Plischka ................... 433/166 |
| 4,518,356 A | 5/1985 | Green ...................... 433/102 |
| 4,571,183 A | 2/1986 | Nash ........................ 433/116 |
| 4,681,541 A | 7/1987 | Snaper ..................... 433/165 |
| 4,684,346 A | 8/1987 | Martin ..................... 433/166 |
| 4,731,019 A | 3/1988 | Martin ..................... 433/119 |
| 4,830,615 A | 5/1989 | Goldstein et al. .......... 433/166 |
| 4,836,780 A | 6/1989 | Buchanan ................. 433/102 |
| 4,850,867 A | 7/1989 | Senia et al. ............... 433/102 |
| 4,886,843 A | 12/1989 | Walton ..................... 522/174 |

(List continued on next page.)

FOREIGN PATENT DOCUMENTS

| | | |
|---|---|---|
| EP | 136500 | 4/1985 |
| FR | 2373269 | 7/1978 |
| FR | 2597327 | 10/1987 |
| GB | 2022475 | 12/1979 |
| IT | 1149157 | 12/1982 |
| IT | 1169326 | 7/1983 |

*Primary Examiner*—Kevin Shaver
*Assistant Examiner*—Melba Bumgarner
(74) *Attorney, Agent, or Firm*—Workman, Nydegger & Seeley

(57) ABSTRACT

An apical portion of a root canal is cleaned with an abrading portion of a file that has a taper that is greater than 0.20. Once the apical portion has been cleaned with an abrading portion that is greater than 0.20, such as 0.25, then an endodontic point, such as a gutta percha point can be easily received in the apical portion of the root canal to seal the apex. It is optimal to utilize a set of instruments. All of the instruments may have files with abrading portions that are greater than 0.25. However, only the larger files need have such abrading portions since they are the last to be used when cleaning the apical portion.

24 Claims, 7 Drawing Sheets

U.S. PATENT DOCUMENTS

| | | | |
|---|---|---|---|
| 4,889,487 A | 12/1989 | Lovaas | 433/102 |
| 4,895,146 A | 1/1990 | Draenert | 606/79 |
| 4,971,556 A | 11/1990 | Ritano | 433/102 |
| 4,984,985 A | 1/1991 | Edwardson | 433/123 |
| 4,992,048 A | 2/1991 | Goof | 433/102 |
| 5,017,138 A | 5/1991 | Schilder | 433/102 |
| 5,026,284 A | 6/1991 | Martin | 433/102 |
| 5,219,284 A | 6/1993 | Velvart et al. | 433/102 |
| 5,236,358 A | 8/1993 | Sieffert | 433/119 |
| 5,257,934 A | 11/1993 | Cossellu | 433/102 |
| 5,299,937 A | 4/1994 | Gow | 433/165 |
| 5,326,263 A | 7/1994 | Weissman | 433/224 |
| 5,498,158 A | 3/1996 | Wong | 433/102 |
| 5,503,554 A | 4/1996 | Schoeffel | 433/102 |
| 5,540,766 A | 7/1996 | Castellani | 106/35 |
| 5,605,460 A | 2/1997 | Heath et al. | 433/224 |
| 5,642,998 A | 7/1997 | Riitano | 433/224 |
| 5,658,145 A | 8/1997 | Maillefer et al. | 433/102 |
| 5,735,690 A | 4/1998 | Malentacca | 433/102 |
| 5,752,825 A | 5/1998 | Buchanan | 433/32 |
| 5,775,904 A | 7/1998 | Riitano | 433/102 |
| 5,868,570 A | 2/1999 | Hickok et al. | 433/102 |
| 6,042,375 A | 3/2000 | Riitano | 433/102 |

ENDODONTIC SYSTEMS AND METHODS FOR PREPARING APICAL PORTIONS OF ROOT CANALS WITH A SET OF FILES HAVING LARGE TAPERS

RELATED APPLICATIONS

This application is a continuation-in-part of U.S. application Ser. No. 09/736,729, which was filed on Dec. 14, 2000. This application is also a continuation-in-part of U.S. application Ser. No. 09/753,981, which was filed on Jan. 3, 2001, now issued U.S. Pat. No. 6,390,819, which is a continuation-in-part of U.S. application Ser. No. 09/536,821, which was filed on Mar. 27, 2000, now issued U.S. Pat. No. 6,379,155, which is a continuation-in-part of U.S. application Ser. No. 09/492,566, which was filed on Jan. 27, 2000, now issued U.S. Pat. No. 6,217,335, which is a continuation-in-part of U.S. application Ser. No. 09/325,035, which was filed on Jun. 3, 1999, now issued U.S. Pat. No. 6,059,572. For purposes of disclosure of the present invention, each of the foregoing U.S. patents and applications is incorporated herein by specific reference.

BACKGROUND OF THE INVENTION

1. The Field of the Invention

The present invention is related to the field of endodontistry. More particularly, the invention is related to systems and operating methods for the preparation of root canals for obturation and the subsequent obturating of the root canals. The systems and methods involve the use of instruments which are dedicated to preparing apical portions of root canals for obturation.

2. The Relevant Technology

To preserve a tooth with a pulp that is diseased or is potentially diseased, it is generally necessary to remove as much of the pulp material as is possible from the pulp canal of the tooth, to shape the root canal(s) without excessively weakening the root canal walls, to prevent or minimize the presence of bacteria through the use of irrigants and dressings, and lastly, to clean the walls of the root canal(s) by removing the smear layer created during instrumentation of the root canal(s). These steps are all done to prepare the root cavity for sealing or obturation which involves filling the root canal with biocompatible materials, such as gutta percha, before the pulp cavity is sealed, thereby promoting the healing and functional recovery of the tooth. This procedure is referred to as root canal therapy.

As indicated hereinabove, root canal preparation involves pulp removal, cleaning of the root canal walls and shaping of the canal walls. This is typically achieved through a guided procedure with the use of instruments which are moved either manually, mechanically or by combinations thereof. These instruments are files or bits that are configured to bore and/or cut. Mechanical instrumentation can be achieved through the use of endodontic handpieces coupled to instruments such as files. The endodontic handpieces can impart rotational motion to a file, reciprocal motion by alternately rotating a file clockwise and counterclockwise, sonic movements or ultrasonic movements.

With regard to operating procedures, there are two basic methods from which all of the canal-preparation techniques can be derived. These methods have been interpreted by various authors in an operational context and also in terms of the instrumentation. The primary conventional systems and methods for removing pulp material from the root canal of a tooth are the apico-coronal (step-back) technique and the corono-apical (crown-down) technique. Although these conventional cleaning techniques both rely generally on sequential increases in the diameter of instruments inserted into the root canal. The step-back technique involves the sequential use of instruments by first inserting an instrument all the way down to the apex of the root canal and then using progressively larger and shorter files to clean the root canal. So the step-back technique involves cleaning the root canal from the apex toward the crown. The crown-down technique uses a set of files that are inserted sequentially further and further into the root canal until reaching the apex and then instrumenting along the entire length of the root canal after the apex has been reached. Each technique has its own unique benefits and disadvantages.

Regardless of which system is utilized, they both rely on ISO dimensions in terms of length, tip diameter and taper. In accordance with ISO, 0.02 is the standard taper of instruments used in cleaning the apical portion. What this means is that for every 1 mm of length, the instrument diameter increases by 0.02 mm. After the apical portion has been cleaned, then one or more soft, resilient, needle-like inserts known as gutta percha points are inserted in each root canal branch in order to at least partially seal and fill the root canal. These gutta percha points are also manufactured in accordance with ISO and have a 0.02 taper like the instruments used to shape the apical portion.

The term "gutta percha" refers to a rubbery material derived from natural rubber, typically blended with zinc oxide. This particular rubbery material is preferred because it is compressible, flexible and relatively soft so that it can be used to fill voids within the exposed root canal. The gutta percha points are typically impregnated with other materials such as radiopaque solids, zinc oxide, for its medicinal properties, and other passive or active ingredients as desired.

The gutta percha point or cone is used to seal the apex of the root canal. In order to ensure that the apex has been adequately sealed, a "tug back" seal is formed. That is, the gutta percha cone is first inserted and then removed. If it can be removed with little or no force, the gutta percha point is trimmed to yield a larger diameter tip and reinserted into the ape. This process is repeated until there is "tug back," thus indicating that the fit between the gutta percha point and the apex is sufficiently tight to adequately seal the apex. However, in some instances the "tug back" may occur above the apex. When this occurs, the apex is not sealed and fluids may enter into the root canal through the apex. This can lead to discomfort and in some instances to failure of the procedure.

To overcome this problem, what is needed in the art of endodontic procedures are methods and system which improve the ability of an endodontic point such as a gutta percha point to seal a root canal at the apex of the root canal.

It would be an additional improvement in the art to provide methods and systems that result in a more thorough cleaning of the apical portion of the root canal to ensure that the "tug back" does not occur during the procedure before the apex has been reached.

SUMMARY AND OBJECTS OF THE INVENTION

An object of the present invention is to provide, methods and systems which improve the ability of an endodontic point such as a gutta percha point to seal a root canal at the apex of the root canal.

It is also an object of the present invention to provide methods and systems that provide for a more thorough cleaning of the apical portion of the root canal to ensure that the "tug back" does not occur during the procedure before the apex has been reached.

An additional object of the present invention is to provide methods and systems which enable the apical portion to be cleaned with files having tapers larger than standard instruments having an ISO taper after the portion above the apical portion has been cleaned and shaped.

Finally, it is an object of the present invention is to provide methods and systems that shape the apical portion of a root canal in a manner that enables a narrow cannula to reach as far as need to deliver adhesive resins for use in filling and/or sealing the root after the gutta percha point has been positioned in the root canal.

Some of the features of the invention which enable these objects to be achieved are summarized hereinbelow.

An apical portion instrument is provided that enables an apical portion of a root canal to be cleaned in a manner than enables an endodontic point, such as a gutta percha point to be easily received in the apical portion of the root canal to seal the apex. It is optimal to utilize a set of instruments. Each instrument in the set has a file that is long enough to extend to the apex of the root canal. At least one of the files in the set of instruments has an abrading portion with a taper that is greater than 0.02. Since conventional gutta percha points have a taper of about 0.02, like conventional instruments used to clean the apical portion of root canals, cleaning the apical portion with an abrading portion of a file that has a taper that is greater than 0.02 enables the gutta percha point to encounter significantly less obstacles or resistance when compared with prior art methodologies.

All of the instruments may have files with abrading portions that have the same taper, such as about 0.025. However, as long as the last file used to clean the apical portion is larger than 0.02 then the others can have any suitable taper. In one embodiment, several of the smaller files have abrading portions with tapers that are 0.02 while the larger files have abrading portions with tapers that are greater than 0.02.

The instruments may be used in accordance with any methodology. However, the apical portion cleaning instruments are preferably used after the operative middle portion and the operative coronal portion have been cleaned in conformance with their anatomical shapes. In some instances, it may be necessary to improve access into the apical portion such that an irrigation needle can be deployed to deliver irrigants to the apical portion after the operative middle portion and the operative coronal portion have been cleaned.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings listed hereinbelow.

DETAILED DESCRIPTION OF THE PREFERRED EMBODIMENTS

Figure 1:
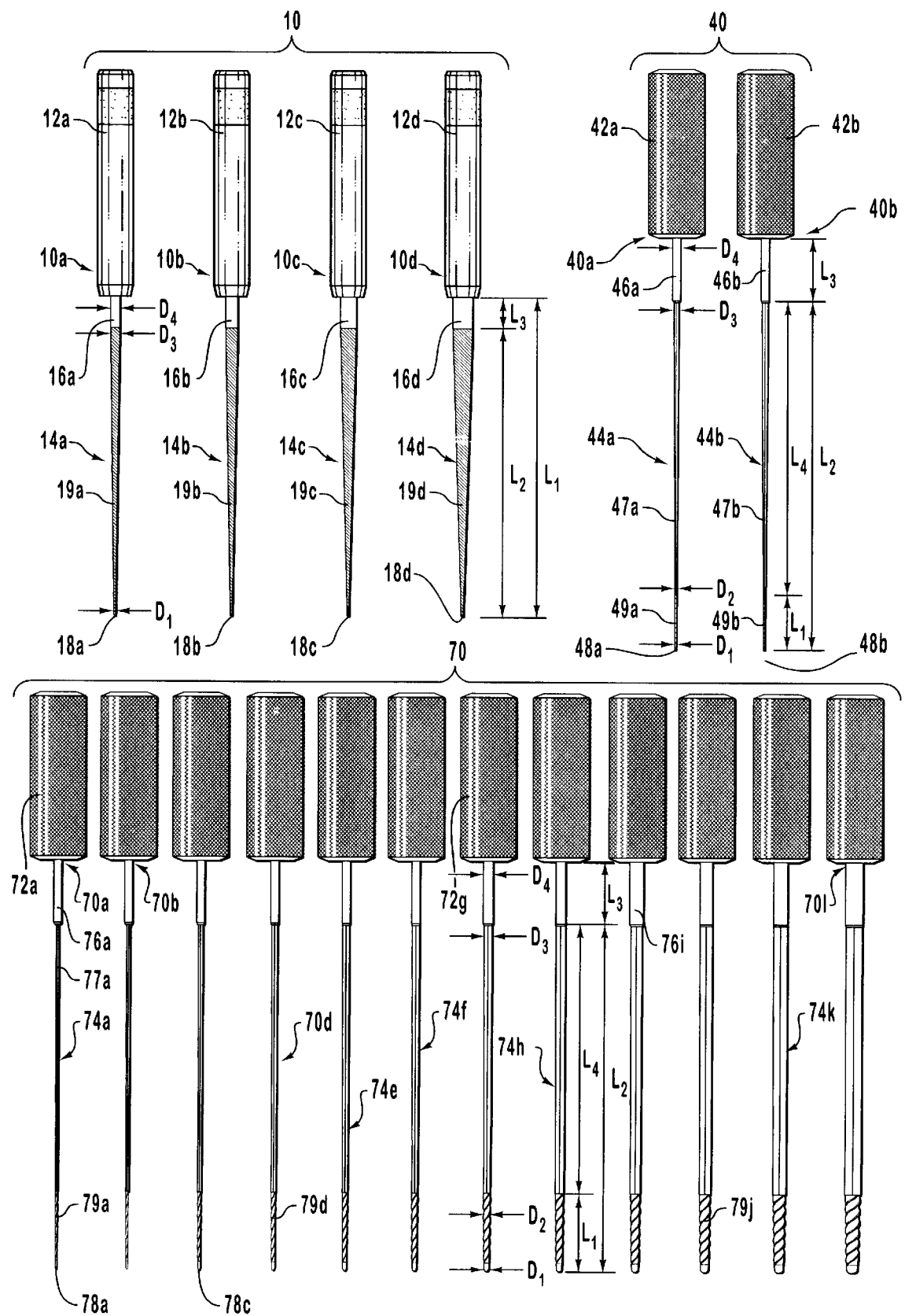
FIG. 1 is a view of a system of endodontic tools including a first set of instruments for cleaning the operative middle portion of an operative root canal, a second set of instruments for improving the access into the apical root portion and a third set of instruments for cleaning the apical root portion.

The present invention relates to a system of endodontic file instruments utilized to clean the apical portion of a root canal. These apical portion instruments have tapers that are larger than conventional ISO tapers. As a result, an endodontic point used to fill the root canal after it has been prepared such as a gutta percha point is more likely to indicate that the fit between the gutta percha point and the root canal is at the apex than at some point above the apex. More particularly, the "tug back" or engagement of the distal end of the gutta percha point with the root canal walls occurs at the apex.

The file instruments used to clean apical portions of root canals that have tapers that are greater than the taper standard set by the International Organization for Standardization (ISO) may be designed, in accordance with the present invention, for use with any methodology used to clean root canals in preparation for obturating the root canal with a material such as a gutta percha point. For example, the file instruments may be used in a step-back methodology or a crown-down methodology as long as the apical portion is cleaned with an instrument that has a greater taper than the gutta percha point that is subsequently inserted during the obturation process. However, the files instruments are preferably utilized in accordance with a unique methodology explained below in detail. Also discussed below, are methods and compositions for filling and sealing a root canal after placement of a single gutta percha point in a root canal that has been prepared and cleaned with a taper that is greater than that of the gutta percha point.

As discussed above, conventional files used in cleaning apical portions of root canals have a taper that is 0.02 in conformance with ISO specifications. Similarly, gutta percha points that are inserted into the root canal once it has been fully cleaned have a taper that is also 0.02 in conformance with ISO standards. It has been found that use of a file instrument having an abrading portion with a taper that is greater than 0.02 or a set of instruments designed for use in series such that at least the last instrument in the set has an abrading portion with a taper that is greater than 0.02 is beneficially utilized with a gutta percha point that has a taper of 0.02. Any file instrument with an abrading portion that has a taper that is sufficiently greater than 0.02 to enable gutta percha points having a taper of 0.02 to be easily inserted to the apex with out prematurely binding is within the scope of the present invention. The taper of such abrading portions may be only 0.0225; however, the taper of the abrading portion is preferably at least about 0.025 in order to ensure that the taper of the apical portion of the root canal is greater along its entire length than the taper of the gutta percha point inserted into the root canal. Accordingly, the taper of the abrading portion of the file of the apical portion instrument is preferably at least about 0.0225, more preferably greater than about 0.0225, and most preferably at least about 0.025.

As indicated above, any instrument is within the scope of the present invention that has an abrading portion with a taper that is greater than that of 0.02 or of the gutta percha point inserted into the root canal. Also such instruments can be used in accordance with any methodology. However, the instruments are preferably part of a system that involves the progressive cleaning of sections of the root canal from the crown to the apex by first cleaning the portion above the apical portion of the root canal and then cleaning the apical portion. This methodology is disclosed in numerous patents and patent applications filed on behalf of Francesco Riitano and owned by Ultradent Products, Inc. of South Jordan, Utah. As explained in detail below, this methodology known as EndoEze® AET™ (Anatomic Endodontic Technology) system owned by Ultradent Products, Inc. enables the instruments to be used in anatomical conformance with the shape of the root canal. U.S. patents that relate to this methodology include U.S. Pat. Nos. 6,045,362 and 6,059,572. U.S. applications related to this technology include U.S. patent application Ser. Nos. 09/492,566; 09/536,821; 09/753,981. Each of the foregoing patents and applications is incorporated herein.

The EndoEze® EndoEze® AET™ (Anatomic Endodontic Technology) of Ultradent Products, Inc. referenced above involves the use of distinct instruments as are shown in FIG. 1 to clean and shape the anatomical root canal in different phases such that the root canal is cleaned progressively and sectionally. The instrument(s) associated with each phase have been designed specifically for that particular phase and accordingly have unique customized characteristics and features. The system of instruments shown in FIG. 1 are described hereinbelow in more detail after explaining the procedures for completing each phase with the different instruments shown in FIG. 1.

Figure 2A:
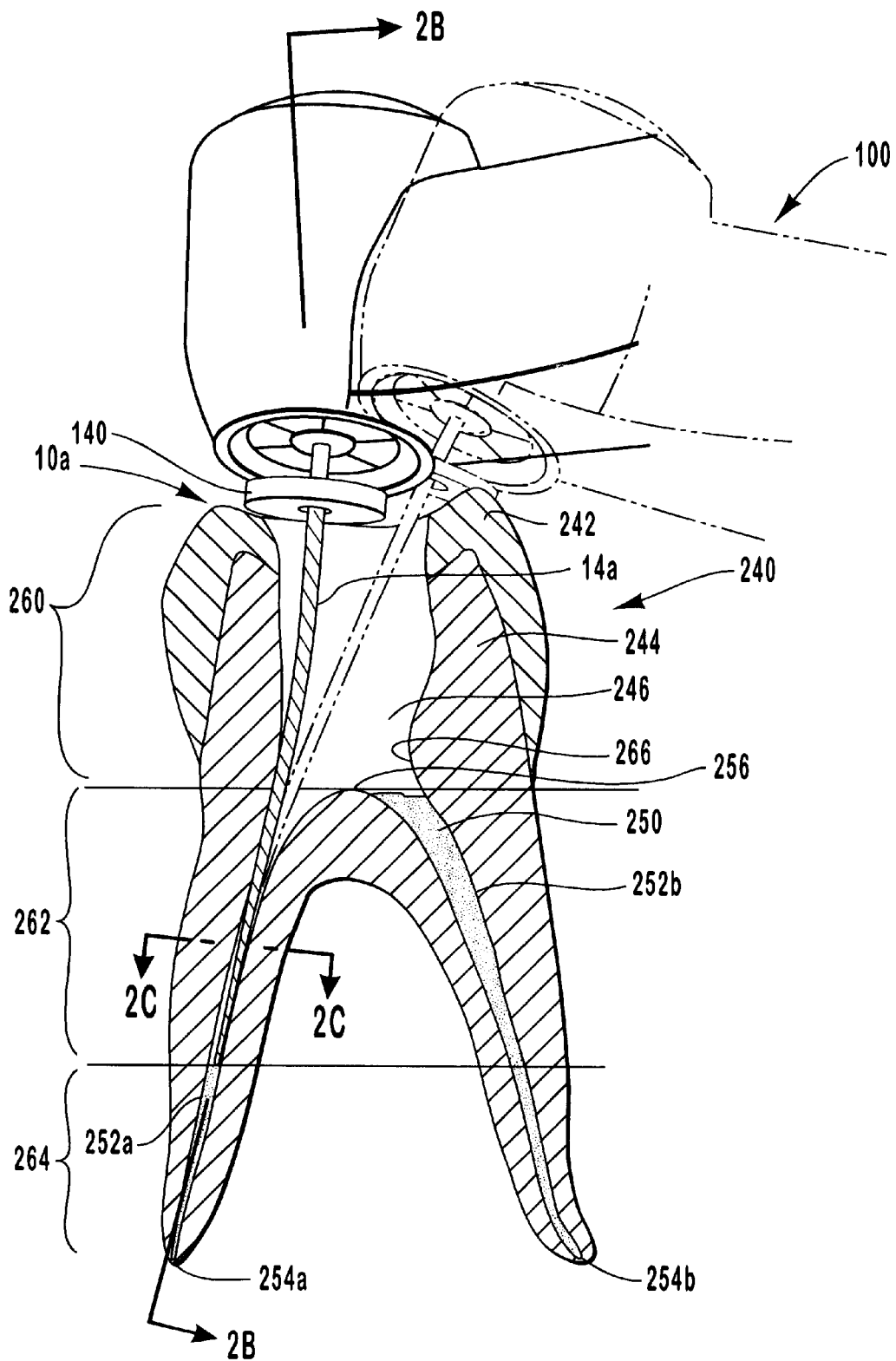
FIGS. 2A–2B show embodiments of endodontic files operated by a driver, such as an electric motor or an air turbine, with lengths that enable the portions of the root canal above the apical portion to be cleaned.

The system of instruments shown in FIG. 1 includes three distinct sets. To appreciate the nomenclature used for these sets, reference is made to FIGS. 2A–2B and 3 which depict a molar 240 in various stages of the root canal cleaning procedure. FIG. 2A depicts a root canal 252a being cleaned after the overhanging portions of enamel 242 and dentin 244 have been removed to provide access into pulp chamber 246 and after the pulp material 250 has been removed from pulp chamber 246. The sections of the operative root canal being cleaned in FIGS. 2A–2B include the operative coronal portion 260 and the operative middle portion 262. The apical portion 264 is shown being cleaned in FIG. 3. The operative coronal portion 260 essentially includes the access cavity walls down to the floor 256 of pulp chamber 246. The operative middle portion 262 is the upper portion of the anatomical root canal while the apical portion 264 is the lower portion of the anatomical root canal. A typical apical portion 264 is the last or bottom 3 mm of the anatomical root canal. For example, the apical portion 264 of root canal 252a extends 3 mm above apex 254a.

Figure 2B:
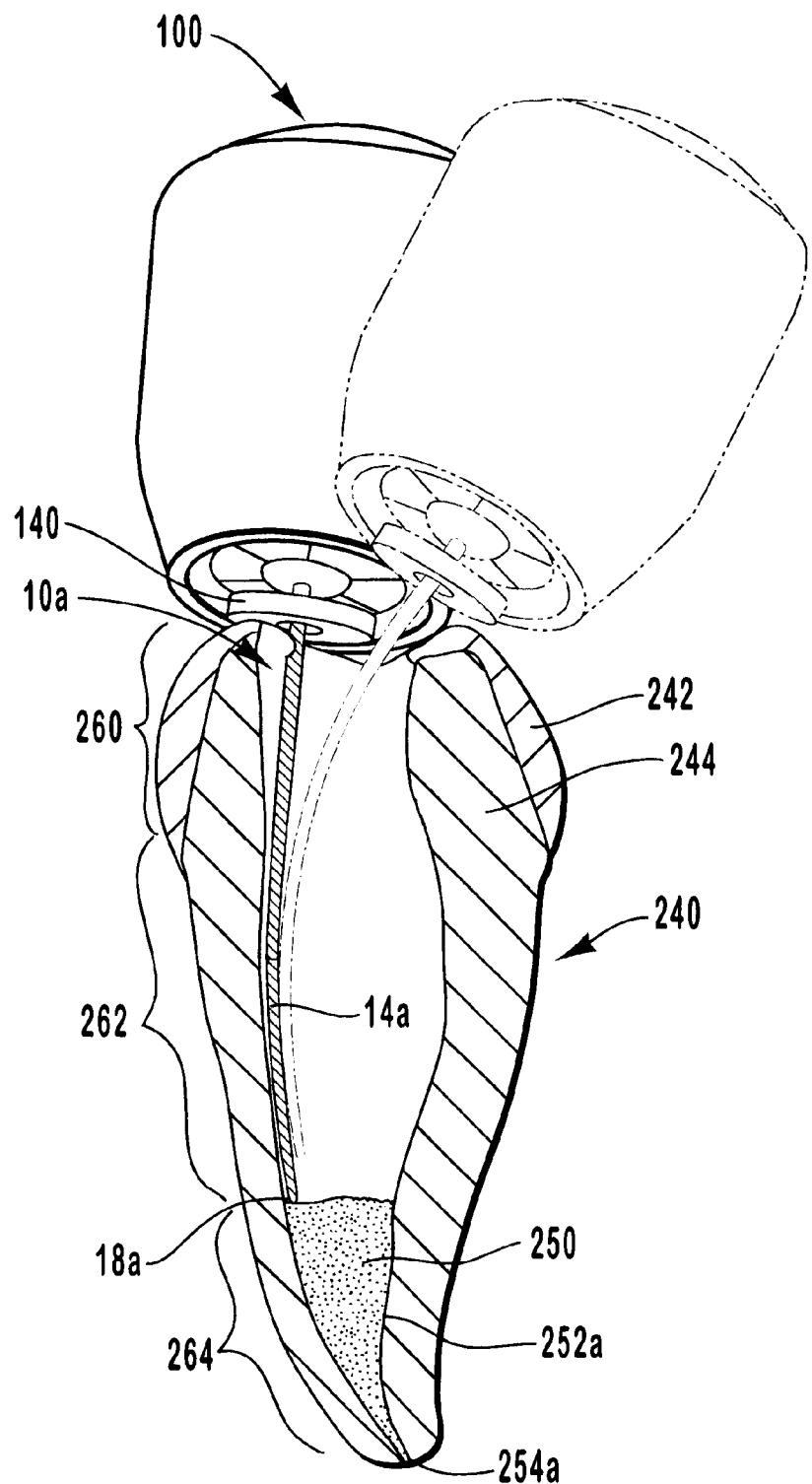
Figure 3:
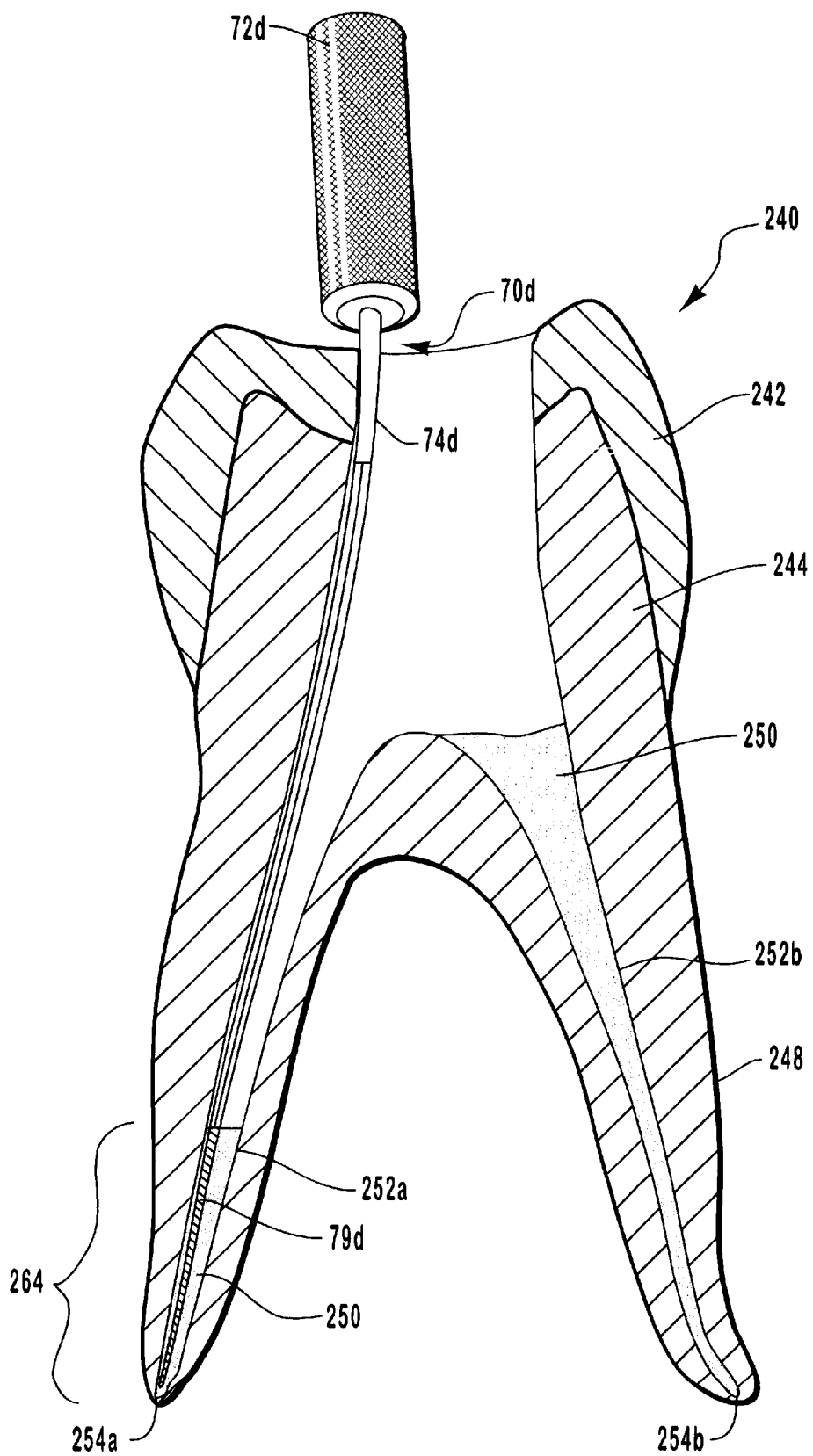
FIG. 3 is a longitudinal cross-sectional view of a tooth with a file inserted into a root canal having a length that is sufficient to reach the apex.

The three distinct set of instruments are namely a set of instruments for cleaning the operative middle portion identified as operative middle portion set 10; an optional set of instruments used to improve access into the apical root portion identified as optional set 40; and a set of instruments for removing and cleaning essentially all pulp material from the apical root portion that is identified as apical portion set 70. FIGS. 2A–2B depict file 14a of instrument 10a from operative middle portion set 10 being used to clean to clean the pulp material from the root canal operative middle portion 262 of tooth 240. Once operative middle portion 262 has been cleaned, then the apical portion 264 is cleaned as shown in FIG. 3 with one of the instruments from apical portion set 70 such as 70d. In some instances, it is necessary to use an instrument from optional set 40 before cleaning the apical portion in order to widen the transition from the operative middle portion 262 to apical portion 264.

The features of each set are provided below in detail in the Example of the Preferred Embodiment. It should be understood, however, that each instrument has a file with a top end extending from a handle. File instruments can also be manufactured that are just a file without a handle. File instrument 10a has a file 14a extending from handle 12a. File 14a has a shank portion 16a and tines or an abrading portion 19a. The abrading portion extends from tip 18a to shank portion 16a. The features of the other files are similarly numbered.

Before utilizing an instrument from set 10, the practitioner first identifies the combined length of the operative middle portion 262 and the operative coronal portion 260. The practitioner then selects a file instrument or a set of file instruments such as set 10 with a file length corresponding to the combined length of the operative middle portion length and the operative coronal portion. After removing the overhanging enamel 242 and dentin 244 with any suitable instrument, file 14a of file instrument 10a is then inserted into root canal 252, as shown in FIG. 2A, down through operative middle portion 262 without extending substantially into apical portion 264. Each file 14 of each file instrument in the set of instruments 10 shown in FIG. 1 has a length that is only sufficient to enable the file to contact the operative middle portion and the operative coronal portion of the root canal. Accordingly, a file instrument such as file instrument 10a or a set of file instruments such as 10 comprises a first endodontic instrument means for anatomically removing and anatomically cleaning essentially all pulp material from the operative middle portion without significantly removing pulp material from the apical root portion.

The file length of files 14a–b enables a practitioner to aggressively clean the operative middle portion without worrying that the instrument will overly thin the root canal, perforate the apex or that cleaning will cause extrusion of material through the apex. Another benefit of cleaning the operative middle portion 262 first is that the apical portion 264 is then generally more accessible and easily cleaned. Additionally, since instruments are selected for use in cleaning the operative middle portion 262 which have files lengths that do not permit entry into the apical portion 264, the likelihood of jamming or breaking a tip of an instrument while working in the confined space of the apical portion 262 is prevented.

By instrumenting in the operative middle portion 262 and the operative coronal portion 260 before the cleaning the apical portion, the practitioner can use an instrument according to the present invention that is relatively flexible compared to the conventional instruments. As shown in FIG. 2B, which is a cross-sectional view taken along cutting line 2B—2B of tooth 240 in FIG. 2A, file 14*a* of file instrument 10*a* is sufficiently flexible to be flexed against any surface of operative middle portion 262 or operative coronal portion 260 and yet is sufficiently rigid to remain flexed against the surface during a cleaning motion such as a longitudinal motion, a rotational motion or a reciprocating rotational motion. The file is also sufficiently resilient that substantial deformation of the file does not occur due to the forces experienced during cleaning of the pulp material from the root canal.

File instrument 10*a* is shown in FIGS. 2A–2B being moved in a longitudinal movement or up and down movement as well as being rotated while file 14*a* is flexed or arched to urge the file against the root canal surfaces. As shown, the configuration and mechanical properties of the files used to clean the operative middle portion 262, and preferably the operative coronal portion as well 260, enable a practitioner to move the files around the perimeter or from side to side to contact the perimeter. Such movements enable the file to follow the contours of the root canal. Further, since the file is moved around the perimeter, the file has more than one center of motion during cleaning of the operative middle portion of the root canal, such as a pivot point or center of rotation, as the tip of the file or at least a part of the abrading portion does not generally remain primarily in one position. Stainless steel is the preferred material for forming the files of the instruments in set 10.

Due mainly to the configuration and mechanical properties of the files, the contours of the operative coronal portion and the operative middle portion can be used during their cleaning by a practitioner as a guide for the movements of the files as the files are pushed against the surfaces of the root canal and simultaneously moved around the perimeter or periphery of the root canal until the practitioner has reached the beginning location of the cleaning and shaping process. By adapting to the perimetrically or perimetral anatomy of the root canal, the entire perimeter or substantially all of the perimeter is contacted and cleaned along the length of the perimeter without substantially altering the configuration of the perimetrically anatomy. For example, in root canals that are primarily noncircular, the files can be urged along one side and then along the next side wall in a manner such that the resulting cleaned and shaped root canal is generally widened but still primarily noncircular. In other words, there is essentially no borehole that obviously corresponds to the shape of the file. Also since a perimetrically anatomy that was primarily tubular or laminar will be enlarged but will still be primarily tubular or laminar, the tooth is less likely to be weakened as compared with prior art methodologies.

Due to the ability to move the file as discussed, the anatomy of the root canal remains substantially unaltered despite the cleaning of essentially all pulp material from the operative middle portion. The understanding that the final anatomy is guided by the shape of the original anatomy enables a practitioner to more confidently urge a file such as file 14*a* against all surfaces of root canal 252 and aggressively clean all of the surfaces of operative middle portion of the root canal since the likelihood of overly thinning the root canal or causing lateral perforations is diminished.

Another advantage of the configuration and mechanical properties of operative middle portion instruments, such as file 14*a* shown in FIGS. 2A–2B, is that the file can simultaneously abrade both operative coronal portion 260 and operative middle portion 262. The files can simultaneously abrade both portions as each file has an abrading portion along the entire length of the file. A primary benefit of simultaneously abrading both portions is the ability to further straighten the operative coronal portion 260 while cleaning the operative middle portion 262.

Use of files in the operative middle portion which have an abrading portion along their entire length or along substantially all of their length such as abrading portions 19*a*–*d* is in contrast to files formed in accordance with ISO standardization. ISO standardized files have abrading portions of up to 16 mm and the remainder of the file is a smooth shank. Since such files are inserted down to the apex, it is generally not possible to abrade any portion beyond the anatomical root canal. Additionally, since such ISO standardized files frequently fail to remove interferences extending from the access or root chamber above the anatomical root canal, the instrument that is manufactured with conventional materials must bend around the interferences, thereby further increasing the likelihood of wall perforations, overthining and failing to clean significant portions of the canal. It especially increases the likelihood of iatrogenic modifications resulting from the tip of the file.

File instrument 10*a* is preferably used in conjunction with an endodontic handpiece designed for movement of endodontic file instruments as shown in FIGS. 2A–2B at 100. The endodontic handpiece 100 and file 10*a* are drawn in phantom lines to represent the ability of the file to be moved and flexed as root canal 252*a* is cleaned. File instrument 10*a* can be continuously rotated in one direction only or file instrument 10*a* can be rotated in a reciprocating motion such that file instrument 10*a* rotates for example, clockwise for half of a revolution and then counterclockwise for half a revolution. A reciprocating motion is preferred as such motion enables the file to alternately engage material 250 and the walls of the operative middle portion of the root canal in a manner that removes material 250 and to then rotate in the opposite direction such that the file less aggressively engages material 250 and the operative middle portion walls, depending on the file design. Accordingly, rotating file instrument 10*a* in a reciprocating motion minimizes breakage of file 14*a* when file 14*a* encounters a surface that prevents rotation of file instrument 10*a* in a direction that enables cleaning and removal of material 250. File instrument 10*a* can also be vibrated or manipulated by hand. Hand milling is, however, more difficult and time consuming. The optional stop 140 shown being utilized is generally not necessary since the file length can be selected to correspond closely with the combined length of the operative coronal portion and the operative middle portion.

As indicated above, it may be necessary in some circumstances to improve the access into the apical root portion before cleaning the apical root portion of the root canal. More particularly, it may be beneficial or necessary to widen the tract of the root canal to provide access for thin irrigation needles. This may be achieved by widening the transition between the operative middle portion 262 and the apical portion 264 or by widening the entire apical portion such that a thin irrigation needle can access the apical portion as needed. Thin irrigation needles typically have a diameter no smaller than about 0.30 mm so it may be necessary to increase the diameter of portions of the root canal up to about 0.35 mm or even up to about 0.40 mm, particularly within the region of the boundary between the operative middle portion and the apical root portion. Note that the diameter need only be slightly larger than a thin irrigation needle in order to provide adequate access. Improving access into the apical portion not only enables such irrigation needles to move as needed, it also reduces the likelihood that the thin irrigation needs will be blocked. Although FIG. 3 depicts file 74d inserted into apical portion 264 of root canal 252a cleaning the apical portion, use of instruments 40a or 40b of optional set 40 is achieved in essentially the same fashion. When utilized to widen the access into the apical root portion of a root canal, file 40a is first introduced followed sequentially by file 40b. A file instrument such as file instrument 40a or a set of file instruments such as 40a and 40b comprises a second endodontic instrument means for improving access into the apical root portion after the pulp material has been essentially removed from the operative middle portion by the first endodontic instrument means.

Set 70 is shown with twelve instruments. However, in use only 1–3 instruments are typically utilized. If a file is inserted and it is apparent to the practitioner that the file is not engaging the walls of the root canal in the apical portion, then a larger file is inserted. While instrumenting the root canal with only this instrument may be sufficient, it is often necessary to utilize one or two additional instruments with successively larger files. So for example, if file 70b or 70c is first introduced into the apical root portion then it is followed by then next larger file such as 70c or 70d.

The dimensions of the files 70a–l are provided below in detail in the Example of the Preferred Embodiment. Note that all of the abrading portions 79a–l may have the same taper or a set may include files with abrading portions having different tapers. However, the last file used to instrument in the apical portion has a taper that is greater than the conventional ISO taper of 0.02 to enable the gutta percha points to be easily inserted. For example, as described in detail in the Example of the Preferred Embodiment, the first several files may have abrading portions with a conventional ISO taper of 0.02 while the remainder have a taper of 0.025. Alternatively, all of the files may have abrading portions with a taper that is about 0.025 or greater than about 0.025.

Use of a file with an abrading portion having a taper that is greater than 0.02 may be considered to be slightly more aggressive than use of a file with an abrading portion having a taper that is 0.02. While it is safe to utilize files with abrading portions having tapers that are greater than 0.02 in the apical portion of a root canal in accordance with conventional methodologies such as the step-back methodology or the crown-down methodology, it is preferred to use such apical files after the operative middle portion 262 has been cleaned, as described above.

The apical portion, as discussed above, is the location in the root canal of most complications that occur during a root canal cleaning procedure. The greatest likelihood for the occurrence of complications such as over thinning of root canal walls, perforation or extrusion of material from the canal is in the apical portion. The apical portion is the most likely site for such complications as apical portions are more complex and delicate compared to the operative middle portions of teeth. Since such complications are most likely to occur in the apical portion, it is highly beneficial to make it easier to clean the apical portion by first cleaning the operative middle portion.

Additionally, it is highly beneficial to have the material removed from the operative middle portion in order to minimize the amount of material that can come out of the root canal to cause problems. Since the majority of bacteria in an infected root canal is typically located in the operative middle portion, removal of pulp material 250 from operative middle portion 262 removes the majority of bacteria in the pulp canal. Not only is the greatest volume of bacteria in the operative middle portion but it is also believed that the concentration is greater in the operative middle portion. Since a certain minimum threshold must generally be reached for complications to arise due to microbial presence in a root canal, removal of the pulp material in the operative middle portion before cleaning the apical portion significantly reduces the likelihood of complications such as exposing the surrounding tissue to bacteria due to overly thinning the root canal, perforation or extrusion of material from the canal. For example, in the event of an apical extrusion far less septic material may be expressed during instrumentation in accordance with present methodology than if the apical extrusion occurred as a result of cleaning in accordance with conventional methods wherein files are inserted to the apical portion before cleaning the operative middle portion. As a result, removal of the majority of bacteria before cleaning the apical portion increases the likelihood of successful root canal therapy in several ways compared with conventional methods. More particularly, since the aggressive cleaning motions do not occur in the apical portion, the likelihood of complications is decreased and if a complication does occur in the apical portion it is less likely to result in failure of the procedure.

So while use of a file with an abrading portion having a taper that is greater than 0.02 may be considered to be more aggressive than use of a file with an abrading portion having a taper that is 0.02, when utilized after the operative middle portion 262 has been cleaned there is little if any increased risk of failure due to complications arising from the use of a larger taper apical file. Further, since the larger taper enables the gutta percha to be positioned in the apex with greater certainty that the apical foramen is closed, the use of the present invention decreases the risk of failure due to complications such as infections.

Each file instrument 70a–l comprises a handle 72a–l connected to a file 74a–l. Each file 74 has a top end where the file joins handle 72. Each file terminates at a tip 78a–l located opposite the top end of the file. Tips 78a–l can have any configuration, however, tips 78a–l preferably have minimal cutting capability to decrease the likelihood of ledging such as the tips shown in FIGS. 8–9. A file instrument such as file instrument 70a or a set of file instruments such as 70a–l comprises a third endodontic instrument means for removing and cleaning essentially all remaining pulp material from the apical root portion after the pulp material has been essentially removed from the operative middle portion.

When cleaning the apical portion 264 as shown in FIG. 3, the apical root portion file instruments are generally moved in a different pattern compared to the operative middle portion file instruments due primarily to the different perimeter anatomies of the two portions. A root canal generally becomes more cylindrical towards the apical portion such that a root canal with a perimeter anatomy that is essentially elliptical in shape within the operative middle portion tapers to an essentially cylindrically shaped perimeter anatomy within the apical portion.

An elliptical perimeter anatomy typically requires that the practitioner move the file around the perimeter and/or flex the rotating file against the surfaces or walls in a milling motion such that the tip is moved to many locations around the perimeter. Due to the more cylindrical anatomy of an apical root portion, it becomes much less necessary, and virtually impossible to flex a rotating file in a milling motion. It is generally adequate to merely rotate the file within the apical root portion and/or move the file in a longitudinal motion. More specifically, after the file reaches the apex or approximately reaches the apex, the file is preferably moved upward while simultaneously being rotated, and it is withdrawn in order to be cleaned before being reintroduced. Since the instruments used to clean the apical portion and to improve the access into the apical portion are typically moved by hand, they have a handle adapted for such use as shown at 42*a*–*b* and 72*a*–72*l* while the instruments 10*a*–*d* used to clean the operative middle portion have handles 12*a*–*d* adapted for use with an endodontic handpiece. The file instruments of the present invention can, however, be utilized with any suitable handle configuration. All of the handles disclosed herein are examples of end means for grasping and operatively moving a file in an abrasive action.

Since an apical portion file is generally not moved around the perimeter as in cleaning the operative middle portion, the center of motion, such as the center of rotation, of the file generally corresponds with the center of the root canal. In contrast, the center of motion during cleaning of the operative middle portion is at various locations as the file is moved around the root canal.

The files used to clean the apical root portion can be designed for primarily longitudinal movement, rotational movement or combinations thereof Since it is generally not necessary to flex a file when cleaning the apical root portion as the apical root portion is typically more round than other sections of a root canal, apical root portion files need not necessarily have the same properties as the operative middle portion files in terms of flexibility, rigidity and resilience. The files used to clean the apical portion are, however, preferably sufficiently flexible to adjust to the anatomy or structure of a root canal in a manner that enables the tip of the file to reach the apex. The files also preferably have sufficient rigidity to apply pressure against the walls or surfaces of the root canal as the abrading portion of the file is urged against the walls of the root canal and simultaneously moved in a cleaning motion even after the file has moved throughout the length of the root canal. Additionally, a file configured for use in an apical root portion preferably has adequate resilience to avoid being substantially deformed as the file passes through a root canal and also as the abrading portion is applied against the walls of the root canal.

The apical portion cleaning instruments are preferably more flexible than the instruments used to clean the operative coronal portion and the operative middle portion since the apical portions tend to be more curved. While stainless steel may be utilized, the files are preferably formed formed from nickel/titanium or a stainless steel alloy such as a precipitation hardenable stainless steel, particularly 17-4PH stainless steel that has not been aged or subjected to heat treatment. While files can be formed from these same metals that are utilized in the operative coronal portion and the operative middle portion, such metals are particularly suited for use in the apical portion as such metals provide optimal flexibility. The instruments used to optionally improve the access into the apical portion may also be formed from any of these metals.

The shapes and dimensions of the embodiments of endodontic file instruments provided herein are merely illustrative, but not limiting, of the variety of endodontic file instruments that are manufactured according to the present invention. Files used to clean the apical portion may have any suitable transverse cross-sectional shape. Any conventional technique may be used to form the files such as twisting a precursor cylindrical rod or blank having three or four sides, cutting lands in a precursor blank or cylindrical rod, abrading the precursor blank or rod to impart a roughened surface, or appropriately machining a precursor blank to form a knurled surface. As a result, the abrading portion may appear like conventional K-files or Hedstrom-type files. The files preferably, however, are configured in a manner such that the potential for breakage is minimized. For example, a file with a square cross-section may be preferred over a triangular cross-section as the file with a square cross-section has a greater mass and is accordingly less likely to break. Additionally, a file configured with tines or extensions having wide angles are generally preferred over those with narrow angles. However, the preferred tine configuration depends primarily on the particular use as in some instances it is desirable to aggressively cut while in others the root can be passively cut. When it is more desirable to aggressively cut, it may be preferred for example to utilize a file with relatively narrow tines. All of the files in combination with their respective abrading portions disclosed herein are examples of means for removing and cleaning of pulp material as the file instrument is operatively moved. Additionally, each abrading portion disclosed herein is an example of a means for abrading a root canal.

Figure 4:
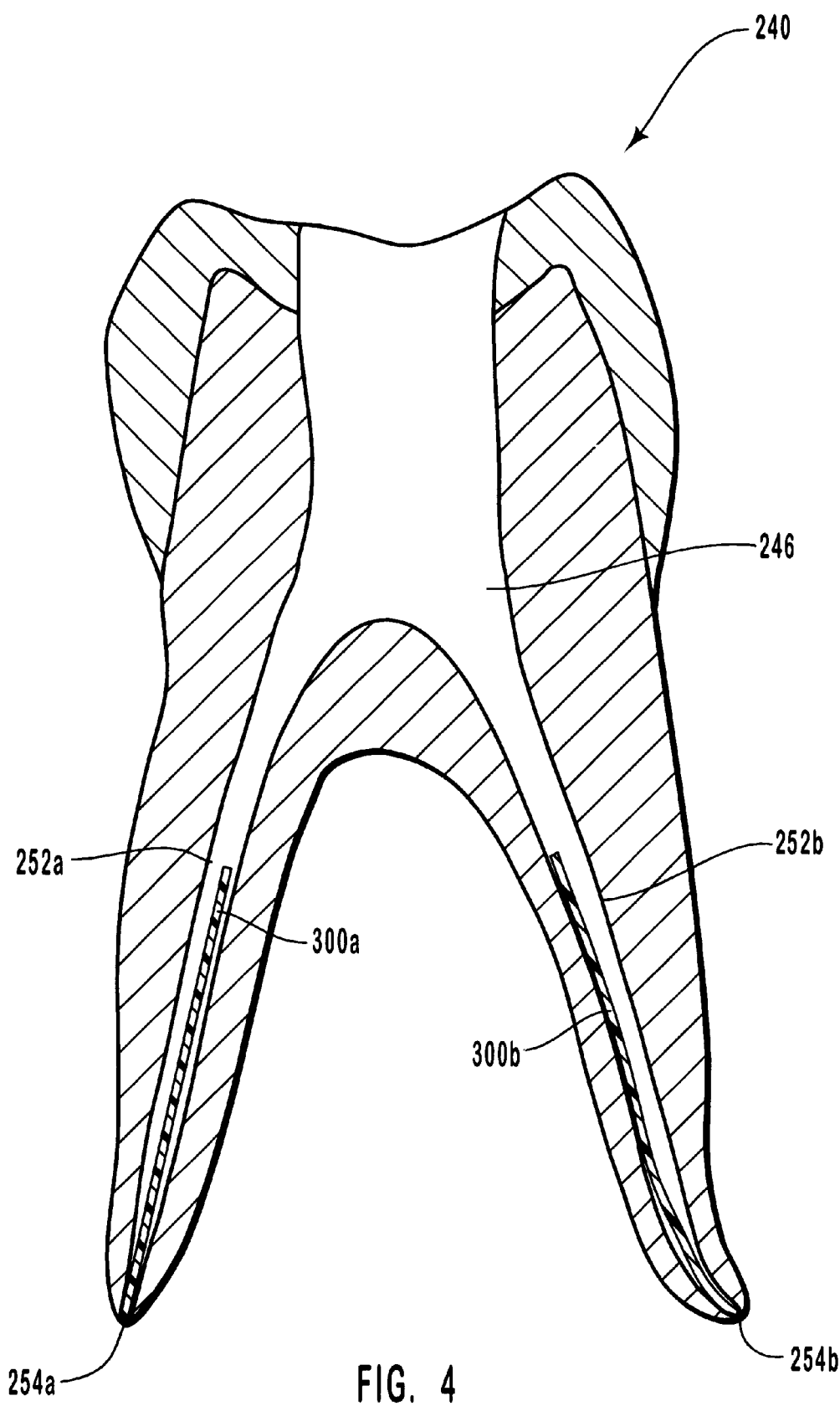
FIG. 4 is a cross sectional view of the tooth 240 showing a root canal with a gutta percha cone inserted into the apex so as to seal the apex and provide a fluid-tight seal.
Figure 5:
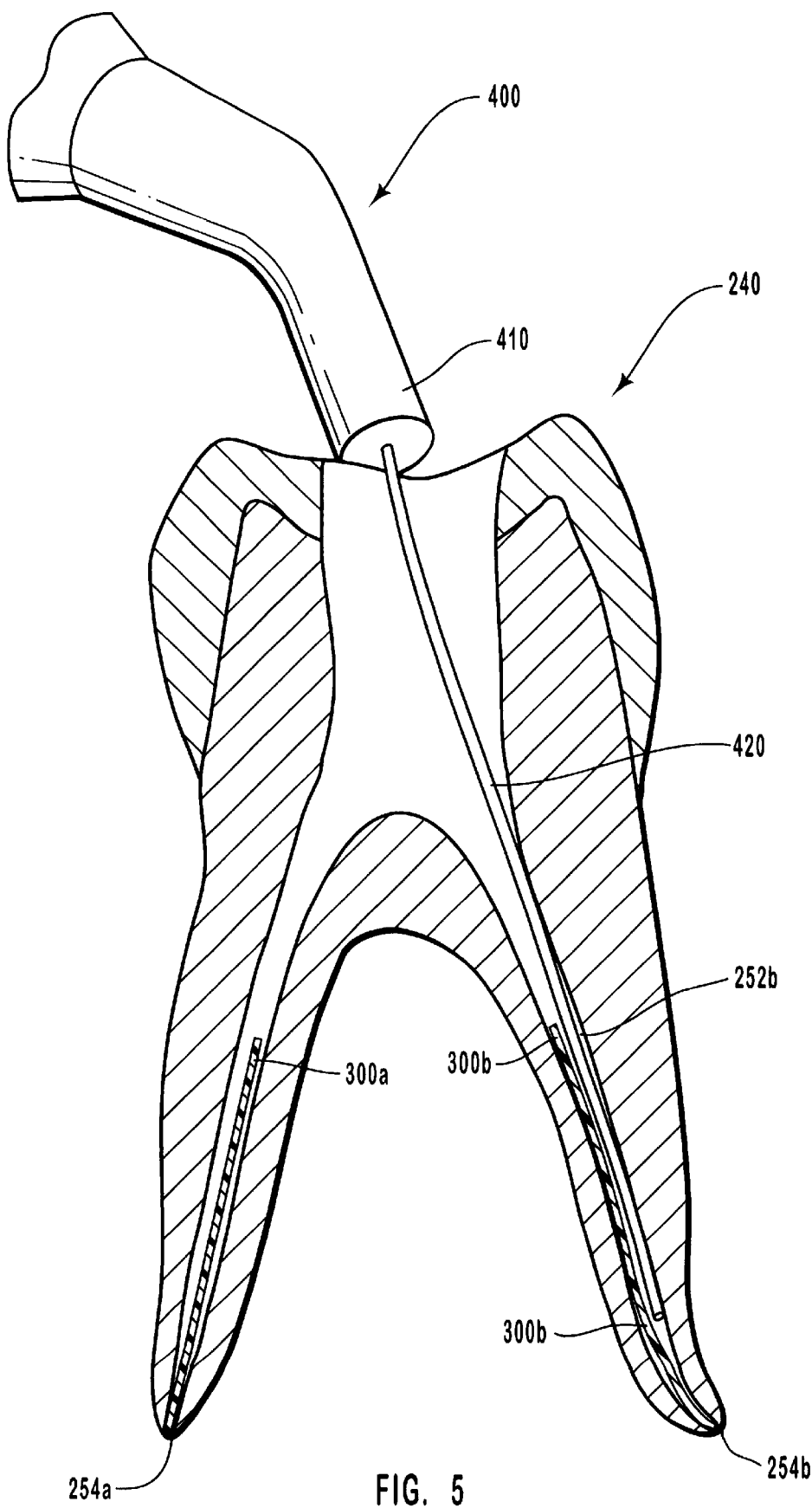
FIG. 5 is a cross sectional view of the tooth 240 in which a small diameter cannula device has been inserted within the root canal for the purpose of filling the root canal with an endodontic sealing or filling resin.
Figure 6:
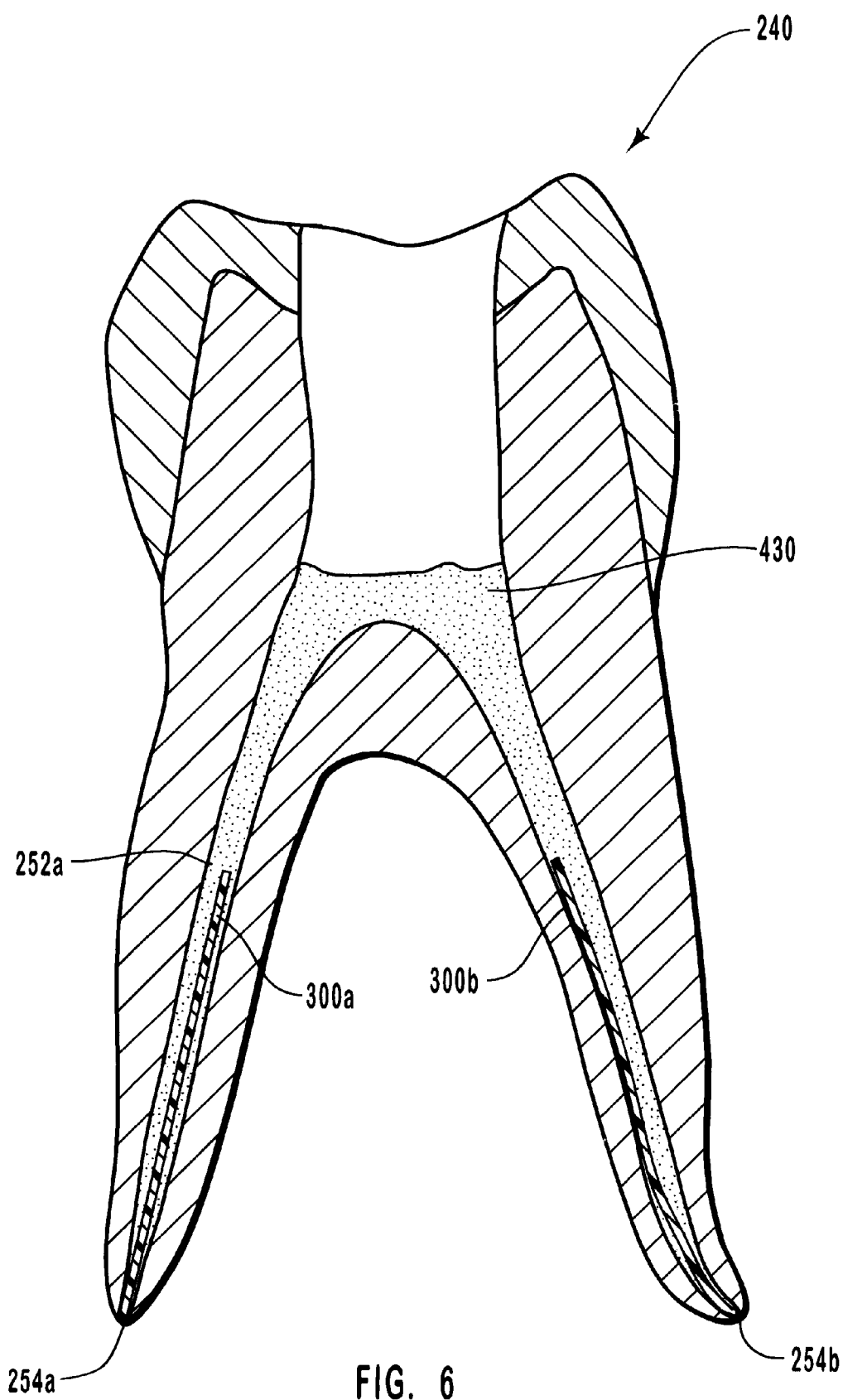
FIG. 6 is a cross sectional view of the tooth 240 after the root canal has been filled with an endodontic sealing or filling resin.

Reference is now made to FIGS. 4–6. FIG. 4 depicts tooth 240 with gutta percha cones 300*a*–*b* inserted into each root canal 252*a*–*b* and into each opening of apices 254*a*–*b* in order to seal the apex 254*a*–*b* of each root canal 252*a*–*b* to prevent flow of sealing material into the surrounding bone tissue.

As discussed above, in order to ensure that each gutta percha cone 300*a*–*b* forms a reliable seal within the respective apices 254*a*–*b*, a procedure involving "tug back" is performed. In this procedure, the gutta percha cone is inserted and removed, sometimes more than one time, to determine how much force is needed to remove the gutta percha cone. If it can be removed with little or no force, there is insufficient tug back, and the gutta percha point is trimmed to yield a larger diameter tip and is reinserted into the apex. This process is repeated until there is sufficient tug back, or resistance, felt by the dentist or dental practitioner. One of ordinary skill in the art of endodontics will know when there is sufficient tug back to confirm an adequate seal of the apex 254*a*–*b* by the gutta percha cones 300*a*–*b*. Sufficient tug back indicates that the fit between the gutta percha cone and the apex is sufficiently tight to adequately seal the apex and prevent flow of sealing or filling material therethrough into the surrounding bone tissue. As discussed above, the apical portion has been cleaned by the file of an instrument with an abrading portion having a taper that is greater than 0.020 while the taper of the gutta percha cone or points 300*a*–*b* has a taper of 0.020 in accordance with ISO. Accordingly, gutta percha cones 300*a*–*b* easily extend to occlude the foramina of the apices as shown.

In addition to the root canals 252*a*–*b*, there are also numerous lateral canals (not shown) that extend from the root canals 252*a*–*b* and provide communication between each root canal 252*a*–*b* and the surrounding periodontal tissue of the lower portion of the tooth 240. The lateral canals are particularly difficult to seal using conventional compositions and methods. Inventive compositions and methods, however, facilitate penetration of resinous sealing or filling material into the lateral canals. Such compositions and methods are disclosed in U.S. patent application Ser. No. 09/736,729 entitled Endodontic Sealing Compositions and Methods for Using Such Compositions which was filed on Dec. 14, 2000 and was previously incorporated by reference.

In a preferred method for placing a resinous sealing or filling material within a root canal, FIG. 5 depicts a syringe tip 400 having a narrow diameter cannula 420 extending from a hub 410 of the syringe tip 400 used to insert sealing or filling material into the root canals 252*a–b*. Due to the narrow opening of the cannula 420, and because typical sealing or filling materials are often sufficiently viscous that they may not readily pass through the cannula 420, it is generally advantageous for the syringe tip 400 to be attached to a high pressure injection system (not shown). An example of high pressure injection system is the hydraulic syringes or systems set forth in copending U.S. patent application Ser. No. 09/742,516 entitled Hydraulic Syringe and Method of Manufacture, filed Dec. 20, 2000. Examples of narrow cannulas sized for entry into a root canal are set forth in U.S. Pat. No. 6,079,979, which is assigned to Ultradent Products, Inc. For purposes of disclosing hydraulic pressurizing systems and cannulas sized to fit within a root canal, the foregoing patent application and patent are incorporated herein by specific reference.

The tip of the cannula 420 is initially placed within one of the root canals 252*a–b* near its respective apex 254*a–b*, and then sealing or filling material (not shown) is expressed therefrom into the root canal 252*a–b*. As the resinous material begins and continues to fill up the root canal 252*a–b*, the cannula 420 is slowly raised or withdrawn from the root canal 252*a–b*. This manner of filling the root canal 252*a–b* with resinous material minimizes or eliminates the formation of air pockets or bubbles as the resin is progressively placed within the root canal 252*a–b*. This procedure greatly improves the ability of the resin to initially purge most or all of the air from within the root canal 252*a–b* compared to simply dipping a gutta percha point in the resin and stuffing the point into a root canal, as is conventionally done. Note that due to the width of each root canal, cannula 420 is able to extend within the root canals along side each gutta percha point 300*a–b* and be withdrawn as the material is delivered instead of just expressing the material in from the top of the root canal.

FIG. 6 depicts a tooth 240 into which a resinous sealing or filling material 430 has been successfully placed within the root canals 252*a–b*, with little or no formation of air pockets. The methodology of cleaning the operative middle portion before cleaning the apical portion, positioning a single gutta percha cone or point to seal the root canal at the apex and then filling the root canal around the gutta percha point is preferred. However, as mentioned above, other methodologies may be utilized to clean the root canal as long as the last file used to clean the apical portion has an abrading portion with a taper that is greater than 0.02. Additionally, conventional methods for placing gutta percha points into the root canal may also be utilized after the apical portion has been cleaned with a is cleaned with a file having an abrading portion with a taper that is greater than 0.02. For example, a single gutta percha point may be dipped in a filling material or several gutta percha points may be pushed into the root canal as is conventionally done.

Preferred compositions for sealing a root canal during an endodontic procedure are disclosed in U.S. patent application Ser. No. 09/736,729 which as referenced above is entitled Endodontic Sealing Compositions and Methods for Using Such Compositions. After the composition is placed around a gutta percha point, then the composition is allowed to polymerize. The polymerization is generally achieved by a chemical initiator in the composition However, a photo-initiator may also be utilized in conjunction with a chemical initiator. The chemical initiator is selected to enable the composition to polymerize in situ after being placed within the root canal.

Examples of the Preferred Embodiments

This example describes, in relation to FIG. 1 and FIGS. 2A–3, an exemplary system and method for cleaning a root canal after the root canal has been properly accessed. After a tooth has been identified as requiring root canal therapy, an x-ray image is obtained in order to determine the state of health of a tooth as well as the structure and anatomical characteristics of the tooth. After all carious tissue has been removed and any old fillings have been infiltrated, a dam is installed.

Before the instruments designed for use in the operative middle portion or the apical portion of the root canal are utilized, the pulp chamber must be properly opened so that adequate access can be gained to the anatomical root canal. Access is gained by removing the top of the pulp chamber, preferably with an appropriate diamond bur instrument. The contents in the pulp chamber are then removed with the aid of appropriate irrigants. Examples of appropriate irrigants include hydrogen peroxide, primarily for use in the canals of living teeth, or sodium hypochlorite, primarily for the canals in necrotic teeth. If desired a cuspidectomy may be performed.

It is then preferable to remove or reduce dentinal or enamel protrusions or irregularities such as dentinal shelves, that may obscure or hinder access of instruments into the operative root canal by rectification of such protrusions with an appropriate instrument which preferably utilizes diamonds for abrasion. Rectification enables an instrument to be inserted in a relatively straight manner though the operative coronal portion 260 and the operative middle portion 262. Since the apical portion of root canal 252*a* is essentially straight, rectification of dentinal shelf 266 above root canal 252*a* would also enable an instrument to be inserted up to apex 254*a* through the apical portion 264 in an essentially straight configuration. Although, an instrument would need to flex within the apical portion 264 of root canal 252*b* due to its curvature, the required flexing is minimized as a result of the removal of dentinal shelf 266 above root canal 252*b*.

After any necessary rectification, the working length is determined for the files used to clean the operative middle portion. The appropriate working length is determined by radiographically identifying the length of the operative root canal and then subtracting 3 mm from the length identified from the x-ray image. It is necessary to subtract 3 mm from the overall x-ray length in order to compensate for any distortions in the x-ray image and to avoid interfering with the apical portion while the operative middle portion is being prepared. After identifying the length of the root canal of a tooth and determining the working length of the files to be used, instruments can then be selected which have a length such that essentially all pulp material can be anatomically cleaned from the operative middle portion of a root canal without significantly removing pulp material from the apical root portion.

As discussed above, FIG. 1 depicts three sets of instruments identified at 10, 40 and 70 which are used to prepare a root canal. As also discussed above, the sets of instruments identified respectively at 10, 40 and 70 are respectively used to clean the operative middle portion, to improve access into the apical portion and to clean the apical root portion.

Operative Middle Portion Phase and Related Sets of Instruments

Tables 1A–1D presented hereinbelow describe the dimensions of four different set of instruments which can be used to clean the operative middle portion in different teeth depending on the particular operative root canal length.

These four sets are preferably sold as part of a kit. Although, the kit includes several sets of instruments, only one set of instruments is typically used for cleaning the operative middle portion. The practitioner selects from several sets in the kit depending on the particular length of the operative coronal portion and the operative middle portion. The instruments in Tables 1A–1D are designed to have a working length that is adjustable depending on the placement of a stop such as stop or the position of the handle within the chuck of an endodontic handpiece. Accordingly, the working lengths for the instruments in Tables 1A–1D are respectively 15–18 mm, 19–22 mm, 23–26 mm, and 27–30 mm As provided in this example, the instruments having a working length of 19–22 mm as presented in Table 1B are selected for use in a tooth due to the combined length of the operative coronal portion and the operative middle portion of the operative root canal which is in the range of 19–22 mm More particularly, the root canal of the tooth is slightly longer than about 25 mm so the full 22 mm of the working length is utilized. The set of instruments for cleaning the operative middle portion detailed in Table 1B corresponds with the set of instruments shown in FIG. 1 at 10. Since only one set of instruments is used to clean the operative middle portion only one set is shown in FIG. 1 at 10.

TABLE 1A

Operative Middle Portion Instruments (15–18 mm)

| Instrument Number | Total Length of the File ($L_2 + L_3$) | Abrading Portion Length ($L_2$) | Shank Portion Length ($L_3$) | Tip Diameter ($D_1$) | Diameter at the top of the Abrading Portion ($D_3$) | Shank Portion Diameter ($D_4$) | Abrading Portion Taper |
|---|---|---|---|---|---|---|---|
| 10a | 18 mm | 15 mm | 3 mm | 0.10 mm | 0.55 mm | 0.50 mm | 0.025 |
| 10b | 18 mm | 15 mm | 3 mm | 0.13 mm | 0.76 mm | 0.70 mm | 0.035 |
| 10c | 18 mm | 15 mm | 3 mm | 0.13 mm | 1.05 mm | 0.90 mm | 0.051 |
| 10d | 18 mm | 15 mm | 3 mm | 0.13 mm | 1.17 mm | 1.00 mm | 0.058 |

TABLE 1B

Operative Middle Portion Instruments (19–22 mm)

| Instrument Number | Total Length of the File ($L_2 + L_3$) | Abrading Portion Length ($L_2$) | Shank Portion Length ($L_3$) | Tip Diameter ($D_1$) | Diameter at the top of the Abrading Portion ($D_3$) | Shank Portion Diameter ($D_4$) | Abrading Portion Taper |
|---|---|---|---|---|---|---|---|
| 10a | 22 mm | 19 mm | 3 mm | 0.10 mm | 0.65 mm | 0.60 mm | 0.025 |
| 10b | 22 mm | 19 mm | 3 mm | 0.13 mm | 0.90 mm | 0.80 mm | 0.035 |
| 10c | 22 mm | 19 mm | 3 mm | 0.13 mm | 1.14 mm | 1.00 mm | 0.046 |
| 10d | 22 mm | 19 mm | 3 mm | 0.13 mm | 1.45 mm | 1.30 mm | 0.060 |

TABLE 1C

Operative Middle Portion Instruments (23–26 mm)

| Instrument Number | Total Length of the File ($L_2 + L_3$) | Abrading Portion Length ($L_2$) | Shank Portion Length ($L_3$) | Tip Diameter ($D_1$) | Diameter at the top of the Abrading Portion ($D_3$) | Shank Portion Diameter ($D_4$) | Abrading Portion Taper |
|---|---|---|---|---|---|---|---|
| 10a | 26 mm | 23 mm | 3 mm | 0.10 mm | 0.78 mm | 0.70 mm | 0.026 |
| 10b | 26 mm | 23 mm | 3 mm | 0.13 mm | 0.88 mm | 0.80 mm | 0.029 |
| 10c | 26 mm | 23 mm | 3 mm | 0.13 mm | 1.12 mm | 1.00 mm | 0.038 |
| 10d | 26 mm | 23 mm | 3 mm | 0.13 mm | 1.43 mm | 1.30 mm | 0.050 |

TABLE 1D

Operative Middle Portion Instruments (27–30 mm)

| Instrument Number | Total Length of the File ($L_2 + L_3$) | Abrading Portion Length ($L_2$) | Shank Portion Length ($L_3$) | Tip Diameter ($D_1$) | Diameter at the top of the Abrading Portion ($D_3$) | Shank Portion Diameter ($D_4$) | Abrading Portion Taper |
|---|---|---|---|---|---|---|---|
| 10a | 30 mm | 27 mm | 3 mm | 0.10 mm | 0.85 mm | 0.80 mm | 0.025 |
| 10b | 30 mm | 27 mm | 3 mm | 0.13 mm | 1.00 mm | 0.90 mm | 0.029 |
| 10c | 30 mm | 27 mm | 3 mm | 0.13 mm | 1.21 mm | 1.10 mm | 0.036 |
| 10d | 30 mm | 27 mm | 3 mm | 0.13 mm | 1.54 mm | 1.40 mm | 0.047 |

When utilized to clean the operative middle portion of a root canal, file 10a is first introduced into the operative middle portion followed by file instrument 10b, 10c and then 10d. Note that, as shown in FIG. 1, the diameter at the top of each abrading portion 19a–d is incrementally greater than the diameter of the top of the abrading portion of the preceding file. Accordingly, the diameter of the top end of each successive file introduced into the operative middle portion is greater than the diameter of the top end of each preceding file. However, the tip diameter of each file in set of operative middle portion instruments are essentially the same. More particularly, the instruments in each set detailed above has a first instrument 10a with a tip diameter of 0.10 mm while the instruments sequentially used thereafter have a tip diameter of 0.13 mm.

Since the tip diameters are essentially equal and since the diameter of the top end of each successive file introduced into the operative middle portion is larger than the diameter of the top end of the preceding file, the taper of each successive file in the set is larger than the preceding file as shown in Tables 1A–1D. Each successive file accordingly has an increased surface area for cleaning the root canal. Additionally, as files are inserted into a root canal with larger and larger tapers, the rigidity of the upper half of each successive file also increases. The increase in rigidity is, however, minimized by maintaining the tip of each file at about the same diameter. The flexibility of the lower half remains essentially constant. The rigidity in the upper half is used to remove interferences and to properly rectify the operative coronal portion 260 and the operative middle portion 262. The consistency in rigidity at the upper half is useful since the lateral perimetrical force applied to the handle is primarily transferred to its upper half or at least the part closest to the handle, which is the strongest part of the file.

By properly selecting a combination of factors including the diameters of the files at the top ends and at the tips as well as the material used to form the files, the files are designed such that each file has sufficient flexibility to be flexed or curved to urge the abrading portion against the surfaces or walls of the root canal and sufficient rigidity to apply pressure against the surfaces of the root canal as the abrading portion of the file is urged against the surfaces of the root canal and simultaneously moved in a cleaning motion. Accordingly, a practitioner can move the instrument around the perimeter of the operative middle portion of the root canal using the contours of the operative middle portion as a guide for the movement of the instrument such that the original anatomy is enlarged and not significantly altered. The operative middle portion instruments in each set are preferably formed from stainless steel.

Apical Portion Widening Phase and Related Sets of Instruments

Tables 2A–2C detail the dimensions of instruments with file lengths which are respectively 21 mm, 25 mm and 30 mm. In this example, the set presented in Table 2B is selected since a tooth is being instrumented with a root canal that is slightly longer than about 25 mm. The set presented in Table 2B is shown in FIG. 1 as set 40.

TABLE 2A

Apical Widening Instruments (21 mm)

| Inst. No. | Total Length of File $(L_1 + L_3 + L_4)$ | Abrad. Portion Length $(L_1)$ | Square Portion Length $(L_4)$ | Round Portion Length $(L_3)$ | Tip Diam. $(D_1)$ | Abrad Portion Diam. $(D_2)$ | Square Portion Diam. $(D_3)$ | Shank Portion Diam. $(D_4)$ | Taper |
|---|---|---|---|---|---|---|---|---|---|
| 40a | 21 mm | 5 mm | 11 mm | 5 mm | 0.08 mm | 0.28 mm | 0.30 mm | 0.80 mm | 0.04 |
| 40b | 21 mm | 5 mm | 11 mm | 5 mm | 0.08 mm | 0.38 mm | 0.40 mm | 1.1 mm | 0.06 |

TABLE 2B

Apical Widening Instruments (25 mm)

| Inst. No. | Total Length of File $(L_1 + L_3 + L_4)$ | Abrad. Portion Length $(L_1)$ | Square Portion Length $(L_4)$ | Round Portion Length $(L_3)$ | Tip Diam. $(D_1)$ | Abrad Portion Diam. $(D_2)$ | Square Portion Diam. $(D_3)$ | Shank Portion Diam. $(D_4)$ | Taper |
|---|---|---|---|---|---|---|---|---|---|
| 40a | 25 mm | 5 mm | 15 mm | 5 mm | 0.08 mm | 0.28 mm | 0.30 mm | 0.90 mm | 0.04 |
| 40b | 25 mm | 5 mm | 15 mm | 5 mm | 0.08 mm | 0.38 mm | 0.40 mm | 1.3 mm | 0.06 |

TABLE 2C

Apical Widening Instruments (30 mm)

| Inst. No. | Total Length of File $(L_1 + L_3 + L_4)$ | Abrad. Portion Length $(L_1)$ | Square Portion Length $(L_4)$ | Round Portion Length $(L_3)$ | Tip Diam. $(D_1)$ | Abrad Portion Diam. $(D_2)$ | Square Portion Diam. $(D_3)$ | Shank Portion Diam. $(D_4)$ | Taper |
|---|---|---|---|---|---|---|---|---|---|
| 40a | 30 mm | 5 mm | 20 mm | 5 mm | 0.08 mm | 0.28 mm | 0.30 mm | 1.1 mm | 0.04 |
| 40b | 30 mm | 5 mm | 20 mm | 5 mm | 0.08 mm | 0.38 mm | 0.40 mm | 1.6 mm | 0.06 |

The files of the instruments in the sets detailed in Tables 2A–2C each have three sections including a smooth shank portion, a square portion and an abrading portion. As indicated above, the set presented in Table 2B corresponds with set 40 shown in FIG. 1. Note, however, with the exception of length, the instruments detailed in Table 2A and Table 2C would appear just like set 40. Instrument 40*a* has a file 44*a* with smooth shank portion 46*a*, a square portion 47*a*, an abrading portion 49*a* and a file tip 48*a*. As shown, the smooth shank portion 46*a* is the top section of file 44*a* and a handle 42*a* is positioned on shank portion 46*a*. Smooth shank portion 46*a* tapers to square portion 47*a* which is between shank portion 46*a* and abrading portion 49*a*.

The smooth shank portion enables stops be positioned on the file to adjust the working length of the file. Each smooth shank portion of each file has a length of about 5 mm with various diameters. The instruments can be used for all operative lengths that are likely to be encountered in clinical practice through the positioning of the stops at the predetermined lengths. While the instruments can be offered in a more expanded series of millimetrically different lengths, the use of stops is acceptable, particularly since, these instruments are manually moved.

In each set, the diameter at the top of the square portion of instrument number 40*a* and instrument number 40*b* is respectively 0.30 mm and 0.40 mm. The abrading portion is formed by twisting the square section so that the abrading portion has a K-file configuration. The instruments in each set all have the same tip diameters. The taper of the files from the tip ($D_1$) to the diameter at the top of the square portion ($D_3$) remains constant and is respectively 0.04 and 0.06 for instrument number 40*a* and instrument number 40*b* in each set.

Preferably, instrument 40*a* is first utilized and then instrument 40*b* to obtain, in a gradual manner, the desired enlargement of the specific transition zone between the operative middle portion and the apical portion. This enlargement is also preferably achieved without significantly changing the diameter of the apical portion of the canal. Accordingly, the tip diameter ($D_1$) of the various instruments in this set remains constant while the diameter at the top of the cutting area or abrading portion ($D_2$), located 5 mm from the tip, is graduated from one instrument to the next, reaching a maximum diameter of 0.38 mm. The rest of the shaft, up to the handle, does not have a cutting surface. To the extent that these instruments are used to expand the apical portion of the canal, the practitioner should constantly bear in mind the average diameters of the canals and the average thicknesses of the parietal walls at the apex.

Note that the entire length of each file can be configured with an abrading portion, however, each abrading portion 49*a–b* preferably extends from tip 48*a–b* along only some of the file. Accordingly, the abrading portion may have any suitable length such as 3 mm or 10 mm; however, the abrading portion in a preferred configuration is about 5 mm or about 6 mm.

As indicated above, the length of a file such as files 44*a–b* is preferably sufficient such that when the file is inserted into the root canal, the tip can at least approximately reach the apex and the abrading portion 49*a–b* of the file can improve the access into the apical portion of the root canal. Although files used to improve the access into the apical root portion may be long enough to approximately reach the apex, the files can be used to improve the access as long as the files can reach the bottom of the operative middle portion and the top of the apical root portion. Such file lengths are typically within a range from about 8 mm to about 35 mm, more typically in a range from about 14 mm to about 35 mm and most typically in a range from about 12 mm to about 33 mm. The length of the abrading portion is generally within a range from about 1 mm to about 35 mm, more preferably in a range from about 2 mm to about 16 mm and most preferably in a range from about 3 mm to about 6 mm. The abrading portion is preferably long enough so that the entire apical portion can be abraded as well as at least the bottom of the operative middle portion.

In a set of instruments used to improve the access into an apical root portion, the file tips of the instruments preferably all have about the same diameter as shown in Tables 2A–2C and in FIG. 1 at 48*a–b*. The diameter of the tips may range from about 0.06 mm to about 1 mm however, the tips preferably have a diameter of about 0.08 mm. In a less preferred embodiment, the tip diameter of each file may also increase sequentially.

As shown in Tables 2A–2C and in FIG. 1, the diameter of the abrading portions 49*a–b* increases from the tips 48*a–b* towards the top of the abrading portions. The diameter of the abrading portion at the top may range from about 0.1 mm to about 0.4 mm and is more preferably in a range from about 0.2 mm to about 0.4 mm. Each successive file has an abrading portion, 49*a*–49*b* which is successively larger in diameter at the top of the abrading portion than the abrading portion of the preceding file. Accordingly, a set may have files with abrading portions having the following respective top diameters: about 0.2 mm, about 0.25 mm, about 0.3 mm and about 0.35 mm. Each abrading portion in such a set has a different taper. Note that the taper of the smooth or shank portions above the abrading portions also increases sequentially, however, the taper may also remain essentially the same.

Apical Portion Cleaning Phase and Related Sets of Instruments

Again sets of instruments are provided with each set having a different length. Three sets of instruments are described hereinbelow which are designed for removing and cleaning essentially all pulp material from the apical root portion after access into the apical root portion has been improved by a set of instruments such as set 40 detailed in Table 2B. In some instances, the instruments described in this example can also be used to clean the pulp material from the root canal immediately after the operative middle portion has been cleaned by a set of instruments such as the sets presented in Table 1B.

Tables 3A–3C detail the dimensions of instruments with file lengths which are respectively 21 mm, 25 mm and 30 mm. However, please note that only instruments from Table 3B are used in the tooth being cleaned in this example. The set of instruments detailed in Table 3B are shown in FIG. 1 as set 70. Set 70 includes instruments 70*a–l* which respectively correspond with instruments 70*a–l* in the set presented in Table 3B.

The instruments in set 70 have a similar appearance as the instruments in set 40. Instruments 70*a–l* have a handle 72 opposite a file 74. Each file 74 has a smooth shank portion 76 (e.g., 76*a*), a square portion 77 (e.g., 77*a*), an abrading portion 79 (e.g., 79*a*) and a file tip 78 (e.g., 78*a*). The sets of instruments presented in Table 3A and 3C have a similar appearance to instruments detailed in Table 3B and shown at 70, however, the files have different lengths. The taper of the files from the tip ($D_1$) to the diameter at the top of the square portion ($D_3$) is provided in each table.

TABLE 3A

Apical Cleaning Instruments (21 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 70a | 21 mm | 5 mm | 11 mm | 5 mm | 0.10 mm | 0.20 mm | 0.42 mm | 0.50 mm | 0.02 |
| 70b | 21 mm | 5 mm | 11 mm | 5 mm | 0.15 mm | 0.25 mm | 0.47 mm | 0.50 mm | 0.02 |
| 70c | 21 mm | 5 mm | 11 mm | 5 mm | 0.20 mm | 0.30 mm | 0.52 mm | 0.60 mm | 0.02 |
| 70d | 21 mm | 5 mm | 11 mm | 5 mm | 0.25 mm | 0.375 mm | 0.65 mm | 0.70 mm | 0.025 |
| 70e | 21 mm | 5 mm | 11 mm | 5 mm | 0.30 mm | 0.425 mm | 0.70 mm | 0.70 mm | 0.025 |
| 70f | 21 mm | 5 mm | 11 mm | 5 mm | 0.35 mm | 0.475 mm | 0.75 mm | 0.80 mm | 0.025 |
| 70g | 21 mm | 5 mm | 11 mm | 5 mm | 0.40 mm | 0.525 mm | 0.80 mm | 0.80 mm | 0.025 |
| 70h | 21 mm | 5 mm | 11 mm | 5 mm | 0.50 mm | 0.625 mm | 0.90 mm | 0.90 mm | 0.025 |
| 70i | 21 mm | 5 mm | 11 mm | 5 mm | 0.60 mm | 0.725 mm | 1.0 mm | 1.0 mm | 0.025 |
| 70j | 21 mm | 5 mm | 11 mm | 5 mm | 0.70 mm | 0.825 mm | 1.1 mm | 1.1 mm | 0.025 |
| 70k | 21 mm | 5 mm | 11 mm | 5 mm | 0.80 mm | 0.925 mm | 1.2 mm | 1.2 mm | 0.025 |
| 70l | 21 mm | 5 mm | 11 mm | 5 mm | 1.0 mm | 1.125 mm | 1.4 mm | 1.5 mm | 0.025 |

TABLE 3B

Apical Cleaning Instruments (25 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 70a | 25 mm | 5 mm | 15 mm | 5 mm | 0.10 mm | 0.20 mm | 0.50 mm | 0.50 mm | 0.02 |
| 70b | 25 mm | 5 mm | 15 mm | 5 mm | 0.15 mm | 0.25 mm | 0.55 mm | 0.60 mm | 0.02 |
| 70c | 25 mm | 5 mm | 15 mm | 5 mm | 0.20 mm | 0.30 mm | 0.60 mm | 0.60 mm | 0.02 |
| 70d | 25 mm | 5 mm | 15 mm | 5 mm | 0.25 mm | 0.375 mm | 0.75 mm | 0.80 mm | 0.025 |
| 70e | 25 mm | 5 mm | 15 mm | 5 mm | 0.30 mm | 0.425 mm | 0.80 mm | 0.80 mm | 0.025 |
| 70f | 25 mm | 5 mm | 15 mm | 5 mm | 0.35 mm | 0.475 mm | 0.85 mm | 0.90 mm | 0.025 |
| 70g | 25 mm | 5 mm | 15 mm | 5 mm | 0.40 mm | 0.525 mm | 0.90 mm | 0.90 mm | 0.025 |
| 70h | 25 mm | 5 mm | 15 mm | 5 mm | 0.50 mm | 0.625 mm | 1.0 mm | 1.0 mm | 0.025 |
| 70i | 25 mm | 5 mm | 15 mm | 5 mm | 0.60 mm | 0.725 mm | 1.1 mm | 1.0 mm | 0.025 |
| 70j | 25 mm | 5 mm | 15 mm | 5 mm | 0.70 mm | 0.825 mm | 1.2 mm | 1.1 mm | 0.025 |
| 70k | 25 mm | 5 mm | 15 mm | 5 mm | 0.80 mm | 0.925 mm | 1.3 mm | 1.2 mm | 0.025 |
| 70l | 25 mm | 5 mm | 15 mm | 5 mm | 1.0 mm | 1.125 mm | 1.5 mm | 1.5 mm | 0.025 |

TABLE 3C

Apical Cleaning Instruments (25 mm)

| Inst. No. | Total Length of File ($L_1 + L_3 + L_4$) | Abrad. Portion Length ($L_1$) | Square Portion Length ($L_4$) | Round Portion Length ($L_3$) | Tip Diam. ($D_1$) | Abrad Portion Diam. ($D_2$) | Square Portion Diam. ($D_3$) | Shank Portion Diam. ($D_4$) | Taper |
|---|---|---|---|---|---|---|---|---|---|
| 70a | 30 mm | 5 mm | 20 mm | 5 mm | 0.10 mm | .20 mm | 0.60 mm | 0.60 mm | 0.02 |
| 70b | 30 mm | 5 mm | 20 mm | 5 mm | 0.15 mm | 0.25 mm | 0.65 mm | 0.70 mm | 0.02 |
| 70c | 30 mm | 5 mm | 20 mm | 5 mm | 0.20 mm | 0.30 mm | 0.70 mm | 0.70 mm | 0.02 |
| 70d | 30 mm | 5 mm | 20 mm | 5 mm | 0.25 mm | 0.375 mm | 0.875 mm | 0.90 mm | 0.025 |
| 70e | 30 mm | 5 mm | 20 mm | 5 mm | 0.30 mm | 0.425 mm | 0.925 mm | 1.0 mm | 0.025 |
| 70f | 30 mm | 5 mm | 20 mm | 5 mm | 0.35 mm | 0.475 mm | 0.975 mm | 1.0 mm | 0.025 |
| 70g | 30 mm | 5 mm | 20 mm | 5 mm | 0.40 mm | 0.525 mm | 1.025 mm | 1.1 mm | 0.025 |
| 70h | 30 mm | 5 mm | 20 mm | 5 mm | 0.50 mm | 0.625 mm | 1.125 mm | 1.2 mm | 0.025 |
| 70i | 30 mm | 5 mm | 20 mm | 5 mm | 0.60 mm | 0.725 mm | 1.225 mm | 1.3 mm | 0.025 |
| 70j | 30 mm | 5 mm | 20 mm | 5 mm | 0.70 mm | 0.825 mm | 1.325 mm | 1.4 mm | 0.025 |
| 70k | 30 mm | 5 mm | 20 mm | 5 mm | 0.80 mm | 0.925 mm | 1.425 mm | 1.5 mm | 0.025 |
| 70l | 30 mm | 5 mm | 20 mm | 5 mm | 1.0 mm | 1.125 mm | 1.625 mm | 1.7 mm | 0.025 |

After the apical portion has been properly widened, the practitioner selects a set of files having the appropriate length, such as one of the sets presented in Tables 3A–3C. To ensure that the files have an appropriate working length, it may be necessary to place stops around the shank portions of the files identified for example at 76a. The practitioner then selects an instrument from the set identified as having an appropriate length for introduction into the root canal down to the apical portion.

As indicated above, in this example, an instrument is selected from the set detailed in Table 3B, which is shown in FIG. 1 as set 70. After selecting an instrument, the practitioner then determines, based on feel and experience, whether the file is appropriately sized or whether a larger or smaller file is needed. For instance, if the practitioner selects instrument number 70b from the set detailed in Table 3B and shown in FIG. 1 at 70b which has a tip diameter of 0.15 mm and the file binds after insertion, then the practitioner would switch to instrument number 70a which has a tip diameter of 0.10 mm. Similarly, if instrument number 70b is too loose then the practitioner would then switch to instrument number 70c which has a tip diameter of 0.20 mm. The practitioner then uses that appropriately sized instrument to clean the apical portion of the root canal by hand. If the practitioner concludes after using an appropriately sized file, that further instrumentation is still needed within the apical portion then the instrument with the next largest file may be used. It is typically unnecessary to use a third instrument with an even larger file after using a series of two instruments. However, the practitioner may clean the apical root portion with a series of more than two instruments as deemed necessary by the practitioner in order to frilly clean the apical portion. This procedure is followed until an instrument has been used that has an abrading portion with a taper that is greater than 0.02 such as instrument 70d. Abrading portion 79d of file 74d has a taper that is 0.025. If file 74d is the first file inserted into the root canal then it may be necessary to utilize one or more files with larger tip diameters that also have abrading portions with a taper of 0.025.

While some of the files in the sets have abrading portions with tapers that are not identical. It is also within the scope of the present invention, to provide sets of instruments that have files with abrading portions that all have the same taper. For example, the taper of files 74a–l from tip 78a–l to the top end of the abrading portion may be the same. The taper may also increase from file to file. In the method of using such instruments, the common feature is that the last file used to clean the apical portion has a taper that is greater than 0.02 to enable a gutta percha point having a conventional taper of 0.02 to be easily inserted into the root canal as far as is needed to appropriately occlude the apical portion. Since it is generally necessary to use only a few of the instruments in the set, it is preferable that the majority of the abrading portions have tapers that are greater than 0.02. Accordingly, only abrading portions 79a–c have tapers that are 0.02 while the remainder of the abrading portions 79d–l have tapers of 0.025.

Each file 74 of the file instruments designed for cleaning the apical root portion of a root canal is configured to have an abrading portion 79 along at least a portion of the length of file 74. The entire length of each file 74 can be configured with an abrading portion 79, however, abrading portion 79 preferably extends from tip 78 part way upward towards the top end of the file such that the remainder of file 74 is relatively smooth. More particularly, each file is preferably configured with an abrading portion along less than about half of the length of the file and more preferably about one-third of the length between tip 78 and the top end of the file. The abrading portion 79 can have a similar or identical configuration to the abrading portion of the file or files used to clean the operative middle portion of the root canal or the files used to improve the access into the apical root portion.

The length of a file such as apical portion files is sufficient such that when the files are inserted into the root canal the tips can at least approximately reach the apex and the abrading portion of the files can substantially contact and clean the pulp material in the apical portion of the root canal.

Such file lengths are generally within a range from about 8 mm to about 35 mm, more typically in a range from about 14 mm to about 35 mm and most typically in a range from about 12 mm to about 33 mm The length of the abrading portion is generally within a range from about 1 mm to about 35 mm, more preferably in a range from about 2 mm to about 16 mm and most preferably in a range from about 3 mm to about 6 mm.

The diameter of the abrading portion is generally within a range from about 0.06 mm to about 1.4 mm As shown in FIG. 1, each successive file has an abrading portion, identified as 79a–l, which is successively larger in diameter at the top of the abrading portion than the abrading portion of the preceding file.

The diameter of the tips 78a–c of each file are preferably increased incrementally such that each sequentially utilized cleaning instrument has a slightly larger tip diameter than the preceding instrument or the tip diameters may be about equal in diameter. The diameter at the top end of the file is preferably greater than the diameter of the abrading portion ash shown in Tables 3A–3C. However, the diameter at the top end of the file can also be equal to or less than the diameter of the abrading portions or even the tip in some embodiments.

The abrading portion 79 of each file 74 of file instruments 70a–l are preferably formed by twisting a blank so as to form a spiral. However, as discussed above, the blank may be shaped by any suitable method. The abrading portion 79 preferably has few spirals such that the action of abrading portion 79 against the walls or surfaces of the apical portion of the root canal is relatively gentle. Such an abrading portion is less aggressive as fewer spirals results in tines that have a wider angle.

Set 10 and set 40 are preferably disposed after use. However, since only one or two instruments from set 70 are used, it is preferable to replace or clean the instruments used from set 70. All of the sets of instruments described in this example may be sold together as a comprehensive kit or various sets may be grouped together as kits intended for use with teeth of particular lengths. For example, the sets used in the tooth cleaned in this example which are detailed in Table 1B, 2B and 3B may be sold together. Additionally, since set 10 and set 40 are intended to be single use sets these sets may also be sold together as a single use disposable kit.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for cleaning the apical root portion of an operative root canal of a tooth, the method comprising:
   selecting an endodontic point having a taper;
   obtaining at least one apical portion cleaning instrument that has a file with an abrading portion for removing pulp material, the file having a taper that is greater than the taper of the endodontic point; and
   cleaning the apical root portion with the at least one apical portion cleaning instrument by abrading the apical root portion with the abrading portion of the file such that the apical root portion is prepared so as to have a taper that is greater than the taper of the endodontic point.

2. A method as defined in claim 1, further comprising:
obtaining at least one additional apical portion cleaning instrument that has a file with an abrading portion for removing pulp material having a taper that substantially equals the taper of the endodontic point; and
cleaning the apical root portion with the at least one additional apical portion cleaning instrument that has a taper that substantially equals the taper of the endodontic point before cleaning the apical root portion by abrading the apical root portion with the abrading portion of the file that has a taper greater than the taper of the endodontic point.

3. A method as defined in claim 1, wherein the taper of the abrading portion of the apical root portion cleaning instrument is about 0.0225.

4. A method as defined in claim 1, wherein the endodontic point has a taper of 0.02 and wherein the taper of the abrading portion of the apical root portion cleaning instrument is 0.0225 such that the cleaned apical portion of the root canal has a taper that is greater than the taper of the endodontic point, the method further comprising introducing a polymerizable sealing composition into the root canal.

5. A method for cleaning the apical root portion of the operative root canal of a tooth, the method comprising:
selecting an endodontic point having a taper of 0.02;
obtaining a set of apical portion cleaning instruments that each have a file with an abrading portion for removing pulp material, wherein at least one of the apical portion cleaning instruments has an abrading portion with a taper that is greater than the taper of the endodontic point; and
cleaning the apical root portion with one or more of the apical portion cleaning instruments such that the instrument that is last to be used in the apical root portion has an abrading portion with a taper that is greater than the taper of the endodontic point to enable the cleaned apical root portion to more easily receive the endodontic point compared to a cleaned apical root portion having a taper that equals the taper of the endodontic point.

6. A method as defined in claim 5, wherein the file of each instrument in the set of apical portion cleaning instruments terminates at a tip, wherein the tips have different tip diameters and wherein the apical root portion is cleaned by sequentially utilizing apical portion cleaning instruments such that each successive file has a greater tip diameter than that of the preceding file.

7. A method as defined in claim 5, wherein the taper of the abrading portion of the apical root portion cleaning instrument that is used last to clean the apical portion has a taper that is about 0.0225.

8. A method as defined in claim 5, the method further comprising introducing a polymerizable sealing composition into the root canal.

9. A method for performing a root canal procedure, the method comprising:
selecting an endodontic point having a taper of 0.02;
obtaining at least one apical portion cleaning instrument that has a file with an abrading portion for removing pulp material, the file having a taper that is greater than 0.02; and
cleaning the apical root portion with the at least one apical portion cleaning instrument by abrading the apical root portion with the abrading portion of the file such that the apical root portion has a taper greater than 0.02;
introducing the endodontic point into the cleaned apical portion of the root canal.

10. A method as defined in claim 9, wherein the taper of the abrading portion of the apical root portion cleaning instrument is about 0.0225.

11. A method as defined in claim 9, further comprising the step of introducing a sealing composition into the root canal around the endodontic point.

12. A method as defined in claim 11, wherein the sealing composition is polymerizable such that it polymerizes in situ.

13. An endodontic system for preparing an apical root portion of an operative root canal of a tooth, the system comprising:
an endodontic point having a taper; and
an apical portion cleaning instrument comprising a file having a length that is sufficient to extend to the apex of a root canal, wherein the file has an abrading portion extending from a tip of the file upward with sufficient length to enable at least the apical portion of a root canal to be abraded, wherein the abrading portion has a taper that is greater than the taper of the endodontic point such that an apical root portion of a tooth that is cleaned using the apical portion cleaning instrument will have a taper that is greater than the taper of the endodontic point.

14. An endodontic system as defined in claim 13, wherein the taper of the endodontic point is 0.02 and wherein the taper of the abrading portion of the apical root portion cleaning instrument is at least about 0.0225.

15. An endodontic system as defined in claim 13, wherein the taper of the endodontic point is 0.02 and wherein the taper of the abrading portion of the apical root portion cleaning instrument is greater than 0.02.

16. An endodontic system as defined in claim 13, further comprising a polymerizable sealing composition.

17. An endodontic system for preparing an apical portion of a root canal of a tooth comprising:
one or more endodontic points having a taper of 0.02; and
a set including a plurality of apical portion cleaning instruments adapted for cleaning the apical root portion of the operative root canal of a tooth, each instrument in the set having a file with a length that is sufficient to extend to the apex of a root canal, wherein each file has an abrading portion extending from a tip of the file upward with sufficient length to enable at least the apical portion of a root canal to be abraded, wherein the file of at least one of the instruments has an abrading portion with a taper that is greater than 0.02 so that the abrading portion with a taper greater than 0.02 can be used to clean an apical root portion so as to have a taper that is greater than 0.02 to thereby enable the cleaned apical root portion to more easily receive the endodontic point having a taper that is 0.20 compared to a cleaned apical root portion having a taper of 0.02.

18. An endodontic system as defined in claim 17, wherein the taper of the abrading portion of the file of at least one of the instruments is at least about 0.0225.

19. An endodontic system as defined in claim 17, wherein the taper of the abrading portion of the file of at least one of the instruments is at least about 0.025.

20. An endodontic system as defined in claim 17, wherein the file of each instrument in the set of apical portion cleaning instruments terminates at a tip, wherein the tips have different tip diameters and wherein the apical root portion is cleaned by sequentially utilizing apical portion cleaning instruments such that each successive file has a greater tip diameter than that of the preceding file.

21. An endodontic system as defined in claim 17, wherein the file of each instrument in the set of apical portion cleaning instruments has essentially the same length.

22. An endodontic system as defined in claim 17, wherein some of the files of the apical portion cleaning instruments have abrading portions with tapers that are about 0.20 and some of the files of the apical portion cleaning instruments have abrading portions with tapers that are at least about 0.0225.

23. An endodontic system as defined in claim 17, wherein the file of each instrument in the set of apical portion cleaning instruments terminates at a tip, wherein the tips have different tip diameters and wherein the apical root portion is cleaned by sequentially utilizing apical portion cleaning instruments such that each successive file has a greater tip diameter than that of the preceding file; and wherein the apical portion cleaning instruments that have relatively small tip diameters have abrading portions with tapers that are about 0.02 and wherein the apical portion cleaning instruments that have relatively large tip diameters have abrading portions with tapers that are at least about 0.0225.

24. An endodontic system as defined in claim 17, further comprising a polymerizable sealing composition.

* * * * *

UNITED STATES PATENT AND TRADEMARK OFFICE
CERTIFICATE OF CORRECTION

PATENT NO. : 6,585,513 B2
DATED : July 1, 2003
INVENTOR(S) : Dan E. Fischer

It is certified that error appears in the above-identified patent and that said Letters Patent is hereby corrected as shown below:

Title page,
Item [57], ABSTRACT,
Lines 2 and 4, change "0.20" to -- 0.02 --
Line 4, change "0.25" to -- 0.025 --
Line 8, change "are" to -- have tapers --
Line 9, change "0.25" to -- 0.02 (e.g., at least about 0.0225) --
Line 9, after "larger" insert -- diameter --
Line 10, delete "such"
Line 10, after "portions" insert -- having a taper greater than the taper of the gutta percha point --

Column 1,
Line 54, after "thereof" insert -- . --

Column 2,
Line 42, change "ape" to -- apex --

Column 3,
Line 18, change "than" to -- that --

Column 5,
Line 36, delete the second occurrence of "EndoEze®"

Column 6,
Line 9, delete the second occurrence of "to clean"
Line 64, after "before" delete "the"

Column 7,
Lines 41 and 47, change "perimetrically" to -- perimetrical --

Column 9,
Line 23, change "then" to -- the --

Column 10,
Line 32, change "that" to -- when --

Column 11,
Line 23, after "thereof" insert -- . --
Line 47, delete the second occurrence of "formed"

UNITED STATES PATENT AND TRADEMARK OFFICE
CERTIFICATE OF CORRECTION

PATENT NO. : 6,585,513 B2
DATED : July 1, 2003
INVENTOR(S) : Dan E. Fischer

It is certified that error appears in the above-identified patent and that said Letters Patent is hereby corrected as shown below:

Column 13,
Line 51, delete "is cleaned with a"
Line 63, after "composition" insert -- . --

Column 15,
Line 9, after "stop" insert -- 140 --

Column 16,
Line 6, after "mm" insert -- . --

Column 20,
Line 15, change "1 mm" to -- 1 mm, --

Column 21,
Line 36, change "1.0" to -- 1.1 --
Line 37, change "1.1" to -- 1.2 --
Line 38, change "1.2" to -- 1.3 --
Line 44, change "25" to -- 30 --

Column 23,
Line 21, change "frilly" to -- fully --

Column 24,
Line 19, start a new paragraph with "The"
Line 21, change "ash" to -- as --

Signed and Sealed this

Twelfth Day of October, 2004

JON W. DUDAS
*Director of the United States Patent and Trademark Office*